US011424012B1

(12) United States Patent
Rai

(10) Patent No.: US 11,424,012 B1
(45) Date of Patent: Aug. 23, 2022

(54) SECTIONALIZING CLINICAL DOCUMENTS

(71) Applicant: Ciitizen, LLC, San Francisco, CA (US)

(72) Inventor: Peeyush Rai, Palo Alto, CA (US)

(73) Assignee: Ciitizen, LLC, San Francisco, CA (US)

( * ) Notice: Subject to any disclaimer, the term of this patent is extended or adjusted under 35 U.S.C. 154(b) by 159 days.

(21) Appl. No.: 16/565,334

(22) Filed: Sep. 9, 2019

Related U.S. Application Data

(63) Continuation-in-part of application No. 16/432,643, filed on Jun. 5, 2019.

(51) Int. Cl.
*G16H 10/60* (2018.01)
*G06N 20/00* (2019.01)

(52) U.S. Cl.
CPC .............. *G16H 10/60* (2018.01); *G06N 20/00* (2019.01)

(58) Field of Classification Search
CPC ....... G16H 10/60; G06N 20/00; G06F 40/258
See application file for complete search history.

(56) References Cited

U.S. PATENT DOCUMENTS

| | | | |
|---|---|---|---|
| 7,937,338 B2 | 5/2011 | Boguraev et al. | |
| 8,176,414 B1 | 5/2012 | Baluja | |
| 8,738,403 B2 | 5/2014 | Flanagan et al. | |
| 10,032,127 B2 | 7/2018 | Habboush et al. | |
| 10,811,125 B2* | 10/2020 | Bao | G06F 16/35 |
| 11,068,490 B2 | 7/2021 | Eifert et al. | |
| 2004/0194035 A1 | 9/2004 | Chakraborty | |
| 2006/0010145 A1* | 1/2006 | Al-Kofahi | G06F 16/353 |
| 2009/0228777 A1 | 9/2009 | Henry et al. | |
| 2014/0032558 A1* | 1/2014 | Renders | G06K 9/00483 707/740 |
| 2014/0316822 A1 | 10/2014 | Kleeman et al. | |
| 2015/0046182 A1 | 2/2015 | Kinney et al. | |
| 2016/0036408 A1 | 2/2016 | Waks et al. | |

(Continued)

OTHER PUBLICATIONS

Mathieu Garchery, "On the Influence of Categorical Features in Ranking Anomalies Using Mixed Data," Sep. 3-5, 2018, International Conference on Knowledge Based and Intelligent Information and Engineering Systems, (10 pages).

(Continued)

*Primary Examiner* — Evangeline Barr
*Assistant Examiner* — Anthony Michael Balaj
(74) *Attorney, Agent, or Firm* — Sterne, Kessler, Goldstein & Fox P.L.L.C.

(57) ABSTRACT

Techniques for sectionalizing clinical documents are provided. In one set of embodiments, a computer system can, for each page of a clinical document: identify one or more section header candidates in the page and, for each section header candidate, attempt to classify the section header candidate as corresponding to one of a plurality of section types using a first classifier or a second classifier. The computer system can further partition the page into one or more sections based on corresponding section header candidates that have been successfully classified using either the first classifier or the second classifier, where the partitioning includes associating each section with a section type in the plurality of section types in accordance with the classification of the section's corresponding section header candidate. The computer system can then validate, for each section, the section's section type via an analysis of the body of the section.

45 Claims, 22 Drawing Sheets

(56) References Cited

U.S. PATENT DOCUMENTS

| | | | |
|---|---|---|---|
| 2016/0364608 A1 | 12/2016 | Sengupta et al. | |
| 2017/0300635 A1* | 10/2017 | Ganesan | G16H 15/00 |
| 2019/0073354 A1* | 3/2019 | Indenbom | G06F 40/30 |
| 2019/0155989 A1* | 5/2019 | Yasumoto | G06Q 10/10 |
| 2020/0159820 A1 | 5/2020 | Rodriguez et al. | |
| 2020/0364451 A1* | 11/2020 | Ammar | G06K 9/00469 |

OTHER PUBLICATIONS

C.E. Shannon, "A Mathematical Theory of Communication," Jul.-Oct. 1948, The Bell System Technical Journal, vol. 27. (55 pages).

\* cited by examiner

1215 Clinical Statement

FIG. 12B

SECTIONALIZING CLINICAL DOCUMENTS

CROSS REFERENCES TO RELATED APPLICATIONS

The present application is a continuation in part of U.S. patent application Ser. No. 16/432,643, filed Jun. 5, 2019, entitled "SECTIONALIZING CLINICAL DOCUMENTS." In addition, the present application is related to U.S. patent application Ser. No. 16/565,355, filed Sep. 9, 2019, entitled "ENTROPY-BASED IDENTIFICATION OF SECTION HEADER CANDIDATES IN ELECTRONIC DOCUMENTS." The entire contents of these applications are incorporated herein by reference for all purposes.

BACKGROUND

The present disclosure pertains to patient health records, and in particular, to systems and methods for analyzing patient health records and providing structured patient health records for treatment and research, for example.

Computerization of health care has traditionally involved streamlining office operations such as scheduling, order entry, charge capture and the like. Electronic medical records (EMRs)/electronic health records (EHRs) were developed in that context. Namely, to improve back office functions of hospitals and other medical organizations. For example, in EHRs information is typically captured using a wide range of codes and terms useful for managing appointments, prescriptions, charges, and other medical business applications.

There is an abundant amount of information residing in electronic medical records. However, harnessing information in such records for clinical purposes is challenging because clinical information (e.g., information about diagnoses and the like) is typically captured in a narrative form in doctors reports and the like. Improved patient outcomes may be derived from analysis of potentially many aspects of medical information, including intersections between electronic medical records and clinical information embedded in notes, reports, and other narratives.

However, there are many technical and regulatory barriers standing in the way. Extracting deeper meaning and insights from intersections of electronic medical records and narratives requires new technical algorithms and techniques. Additionally, privacy restrictions on medical records makes accessing such records a challenge that only non-patient centric systems have typically been able to overcome. Accordingly, processing such forms of medical information can be challenging, and deriving meaningful results to improve patient outcomes, cure diseases, and save lives remains elusive. A patient centric solution to the above challenges would be highly advantageous.

BRIEF DESCRIPTION OF THE DRAWINGS

FIG. 12B illustrate another example an extracted clinical statement according to an embodiment.

DETAILED DESCRIPTION

In the following description, for purposes of explanation, numerous examples and details are set forth in order to provide an understanding of various embodiments. It will be evident, however, to one skilled in the art that certain embodiments can be practiced without some of these details or can be practiced with modifications or equivalents thereof.

Figure 1:
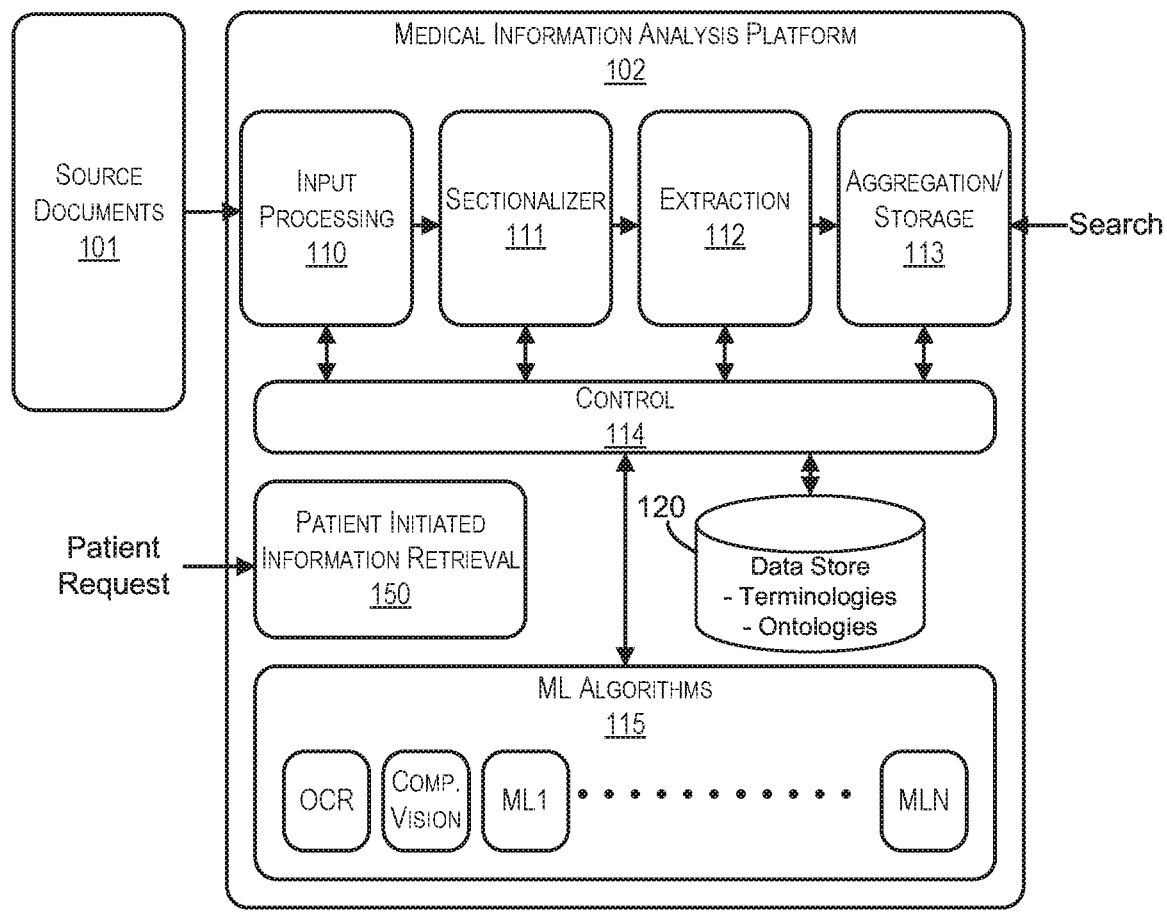
FIG. 1 illustrates a patient health records analysis platform according to an embodiment.

FIG. 1 illustrates a medical information analysis platform 102 according to an embodiment. Features and advantages of the present disclosure include a medical information analysis platform (or system) that may, for example, receive clinical documents comprising one or more narratives of information, process the clinical documents using machine learning (ML) algorithms (e.g., which may be successively more focused), and store information from the clinical documents in a searchable data structure together with other relevant data.

Features and advantages of some example embodiments of the present disclosure include a system where medical information about a patient is received in response to a patient-initiated request. For example, traditionally, hospitals and other medical professional exchange medical information on a patient's behalf since they are more experienced in complying with regulations surrounding the handling of medical records. However, patients have not traditionally been able to control the flow of their own medical information. Features and advantages of some embodiments of system 102 include a patient-initiated information retrieval component 150. Component 150 may receive a patient request and interface with one or more medical organizations/health care providers (not shown) to initiate the retrieval of clinical documents and other medical records for patients, for example, resulting in a patient centric platform that provides patients with a wealth of information about their health, all under the patient's control, for example.

Referring to FIG. 1, clinical source documents 101 may be received in the system 102 in a variety of ways. For example, machine readable clinical documents may be received over email, fax, upload, Fast Healthcare Interoperability Resources (FHIR), or a custom API to name just a few. Clinical documents 101 may first be processed by an input processing block 110. Input processing block 110 may apply different processing steps based on the content of the clinical document received. For example, some clinical documents may undergo optical character recognition (OCR) to extract text from the document, for example, while other documents may be processed with a computer vision algorithm, which may determine various aspects of a medical image, for example, and generate metadata about the image in text form.

Control block 114 may determine which of a plurality of machine learning (ML) algorithms 115 to apply at various stages of processing. ML algorithms 115 may include optical character recognition (OCR), computer vision (e.g., image processing and recognition algorithms), and a variety of different ML algorithms used for sectionalization and extraction. N machine learning algorithms, ML1 . . . MLN (where N is an integer), for sectionalization and extraction are shown here, and examples are described further below. ML algorithms 115 may include ML models (e.g., convolutional neural network models) and natural language processing (NLP) algorithms ML models may be distinguished from NLP algorithms in the sense that an NLP model takes a bag of words and is configured to understand the context around the words and relationships between words, for example, whereas ML models may be more specific and targeted (e.g., ML models may be trained to recognize dates, phone numbers, particular providers, etc.). If a clinical document is a scanned report including a text narrative (or notes) and an image, for example, control block 114 may extract the text using an OCR component and analyze the image using a computer vision component, for example. Input processing block 110 may output text versions of the clinical documents in a standard (or normalized) format for further processing by system 102, for example.

System 102 includes a sectionalizer block 111 that classifies different sections of the clinical documents. Accordingly, in some embodiments, different text in different sections may be processed using increasingly focused ML algorithms, for example. In one embodiment, one or more ML algorithms classify different sections of the clinical documents based on significant signatures corresponding to the different sections. For example, a clinical document may contain headers between bodies of text comprising paragraphs, tables, lists. A first ML algorithm may classify a header as one of a plurality of predefined common clinical concepts/domains as described in more detail below. Advantageously, one or more second ML algorithms may verify classification of a section based on text associated with the sections. For example, one section may be classified by the first ML algorithm as "Lab Results." Advantageously, the text associated with that section may be analyzed by one or more other ML algorithms specifically trained to identify lab report related words or phrases. Accordingly, the one or more second ML algorithms used to analyze a body under the header may be selected from the plurality of ML algorithms 115 based on the classification by the one or more first ML algorithms that analyze the header, for example. As described in more detail below, text associated with different sections having different classifications may be processed using different second ML algorithms. The results of the second ML algorithms (e.g., an NLP trained to analyze lab reports) may be used to verify that the section does, in fact, pertain to lab reports, for example. Accordingly, the section classification may use a combination of 2 strategies to get a confidence score: 1) section heading classification, and 2) section contents classification. Further detailed examples and embodiments of sectionalization are presented in more detail below.

The output of sectionalizer block 111 is text from the clinical document broken down into groups of text and classifications associated with the groups of text (e.g., text from a lab report section of a clinical document and a classification associated with the text indicating that the text is from the lab report section of the document). The text from sectionalizer block 111 is provided to extraction block 112, which may transform text associated with the sections into structured clinical data records. In one embodiment, different words or phrases of text for each section are classified using a plurality of NLP algorithms (e.g., a pipeline). The algorithms used to perform the transformation may be selected based on the classification of each section. For example, text associated with a lab report may be processed with one pipeline of NLPs, and text associated with a cancer procedure may be processed with another pipeline of NLPs. Selecting different NLPs based on different section classifications may improve the accuracy of the results or the amount of information obtained (or both) from the clinical documents, for example. Extraction block 112 may analyze different combinations of classified words or phrases of the text for each particular section and map different combinations to structured clinical data records, for example. Mapping classified words or phrases to the structured clinical data records may include using the classified words or phrases to retrieve additional information stored in data store 120. Data store 120 may store terminologies and/or ontologies, which may be used to supplement the classified words or phrases with codes, for example. Data store 120 may represent multiple data stores including information such as RxNorm, which provides normalized names for clinical drugs and links the names to many of the drug vocabularies and codes, SNOMED (or SNOMED CT), which provides organized computer processable collection of medical terms providing codes, terms, synonyms and definitions used in clinical documentation and reporting, Logical Observation Identifiers Names and Codes (LOINC), which is a database and universal standard for identifying medical laboratory observations, NCI, which provides cancer related ontologies from the National Cancer Institute, and/or customized synonyms or other ontologies, for example. Additional examples of extraction and structured clinical data records (e.g., clinical statements) are described in more detail below.

The output of extraction block 112 is a structured clinical data record. A structured clinical data record may represent clinical entities based on the identified entities in the particular section. Structured clinical data records may comprise a plurality of fields and data associated with the fields, such as a patient ID, date and time, a clinical concept/domain (e.g., procedure, medication, etc. . . . ), a code (e.g., SNOMEDCT_US Code=450436003), and a variety of other fields and data values based on the nature of the document and section/subsection text being analyzed, for example. In one embodiment, structured clinical data records are provided to an aggregation and storage block 113. Aggregation and storage block 113 may store some (or all) of the information from the structured clinical data records in a searchable data structure. Accordingly, a search may be received, which in some example applications may ask insightful questions and obtain previously unattainable or challenging results based on the clinical document processing, extraction, and storage techniques described herein. For example, the search may request all patients who have been off a particular chemotherapy drug for at least three (3) months, which may be a criteria for inclusion in a clinical trial. Answers to the search queries achievable using the techniques described herein empower a wide range of life saving or quality of life improving possibilities.

Figure 2:
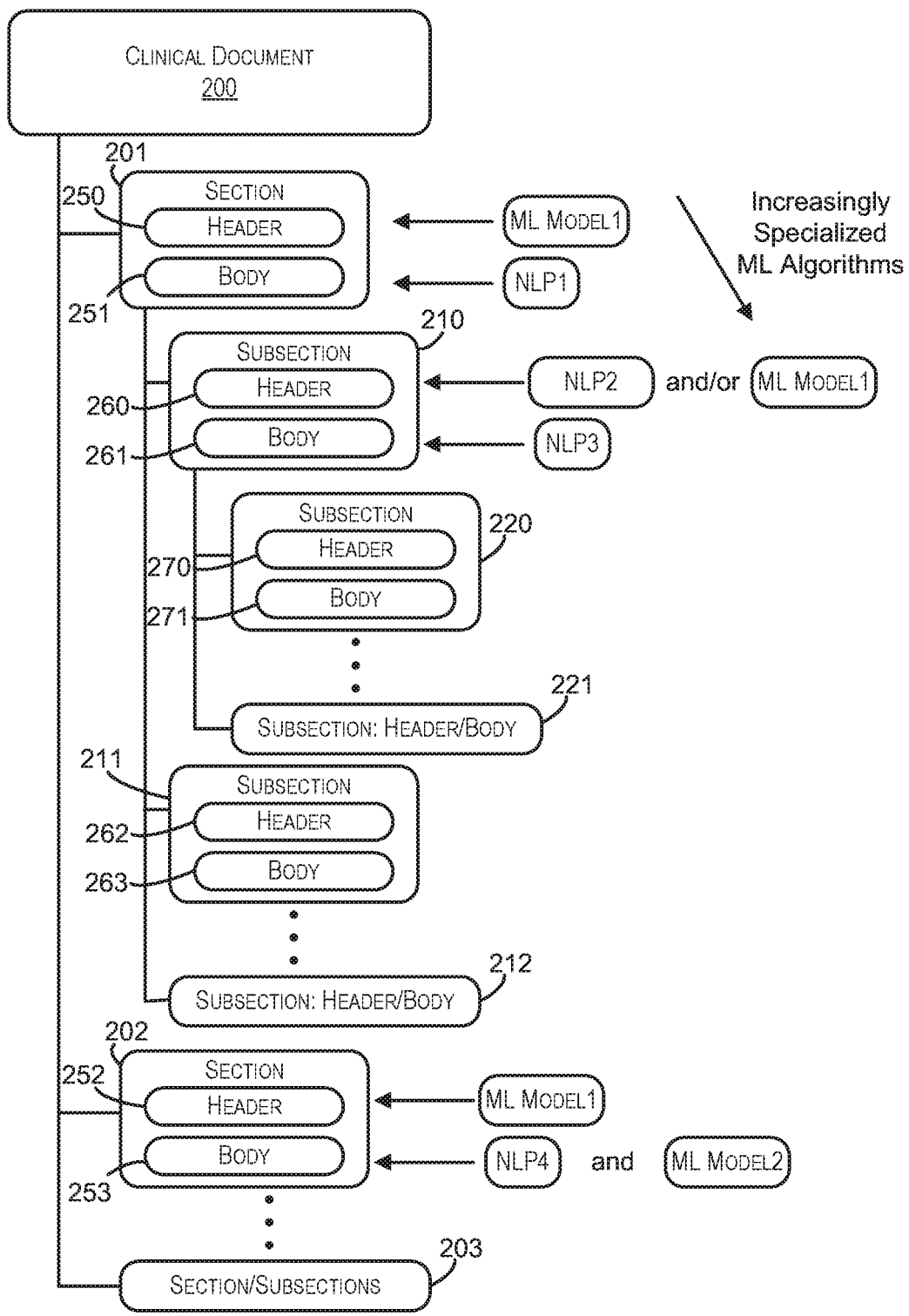
FIG. 2 illustrates applying specialized ML algorithms to sectionalize a clinical document according to an embodiment.

FIG. 2 illustrates applying specialized ML algorithms to sectionalize a clinical document according to an embodiment. In this example, a clinical document 200 may comprise a hierarchy of sections 201-203, subsections 210-212, and subsections 220-221, for example. Embodiments of the disclosure may advantageously apply different and/or more specifically trained ML algorithms to different sections and subsections to more accurately analyze and classify text associated with the different sections and subsections, for example. In this example, a first section 201 may comprise a header 250 and body 251. Header 250 may be analyzed using a first machine learning (ML) model, ML Model1 (e.g., a convolutional neural network), to recognize particular features indicative of a section header, for example. Body 251 may comprise text, for example, which may be analyzed using a first natural language processor (NLP) algorithm, NLP1, for example. As mentioned above, in some embodiments, NLP1 may be selected based on the result produced by ML Model1, and NLP1 may be used to verify the classification of section 201, for example.

For section headings, ML models, such as neural networks, may be used as they are more specific and are trained to recognize a limited set. However, for subsection recognition, a combination of ML model classification and NLP clinical entity recognition may be used since the names may contain pure section headers or clinical entities like "Lab" or "Procedure" names, for example. Thus, in general, one or more ML models or NLP algorithms may be used as needed, depending on the types of section and/or subsection headers being analyzed, for example.

In this example, subsection 210 may comprise header 260 and body 261. As the system analyzes text deeper in the hierarchy, some (or optionally all) of the ML algorithms used may become more focused and targeted (e.g., trained to recognize a narrower category of medical topics). Embodiments of the disclosure may use one or more third ML algorithms to classify different subsections of the clinical documents based on subsection significant signatures corresponding to the different subsections. In this example, header 260 may be processed using either ML Model1 (e.g., because some subsections may include the same information as may be found in sections) or NLP2, or both, for example, to classify subsection 210. NLP2 may be trained to recognize subsection types, such as comments, impressions, etc. . . . or clinical entity types, such as medications, lab work, procedures, diagnosis, vitals, immunizations, allergies, genetic alterations, etc. . . . . . Additionally, one or more fourth ML algorithms may verify the classification of the different subsections based on text associated with the particular subsection. In this example, body 261 is processed using NLP3, which may recognize lab related language if section 201 was classified as pertaining to lab work, for example. In other embodiments, body 261 may be processed with an NLP selected based on the result(s) of the one or more ML algorithms used to process header 260, for example.

In some embodiments, a plurality of ML algorithms may be used to verify classification of a section. For example, ML model1 may analyze header 252 in section 202 and produce a resulting classification. Body 253 may be analyzed by a combination of at least one machine learning (ML) model and at least one NLP algorithm. In this case, body 253 of section 202 is analyzed using an NLP4 and a ML Model2. For instance, if ML Model1 determines that header 252 pertains to demographics of a patient, then classification may use both NLP4 and ML Model2, which may both be trained to recognized demographic information, such as a name. In some cases, demographics information can exist as a stand alone entity (Name: John Smith) or can exist in a sentence (My patient John Smith is a 64 yr old male). Thus, both ML and NLP trained models for demographics may be employed to determine the classification of the body 253, for example. Similar approaches using multiple ML algorithms may be used for other section and/or subsection classifications, for example.

The following is a list of example ML algorithms that may be used to analyze headers and bodies of sections and subsections according to one or more embodiments:

Section Header Classification

Section Header Classification (ML Model)

Subsection Header Classification

Section Header Classification (ML Model) (subsections can also have main section headers)

Subsection Classification (NLP) (these are known sub section types like Comments, Impressions etc.)

Clinical Entity Recognizer (NLP) (recognizes Medications, Labs, Procedures, Diagnosis, Vitals, Immunizations, Allergies, Genomic Alterations etc.)

Entity Recognition—Applied to Bodies During Sectionalization

Clinical Entity Recognizer (NLP) (recognizes Medications, Labs, Procedures,

Diagnosis, Vitals, Immunizations, Allergies, Genomic Alterations etc.)

Cancer Entity Recognizer (NLP)—For cancer specific entities like Stage, Performance, Disease status etc.

Demographic Entity Recognizer (NLP, ML Model)

Provider Entity Recognizer (NLP, ML Model)

Shape Recognizer (ML Model)—recognizes dates, phone numbers, MRN etc.

Figure 3:
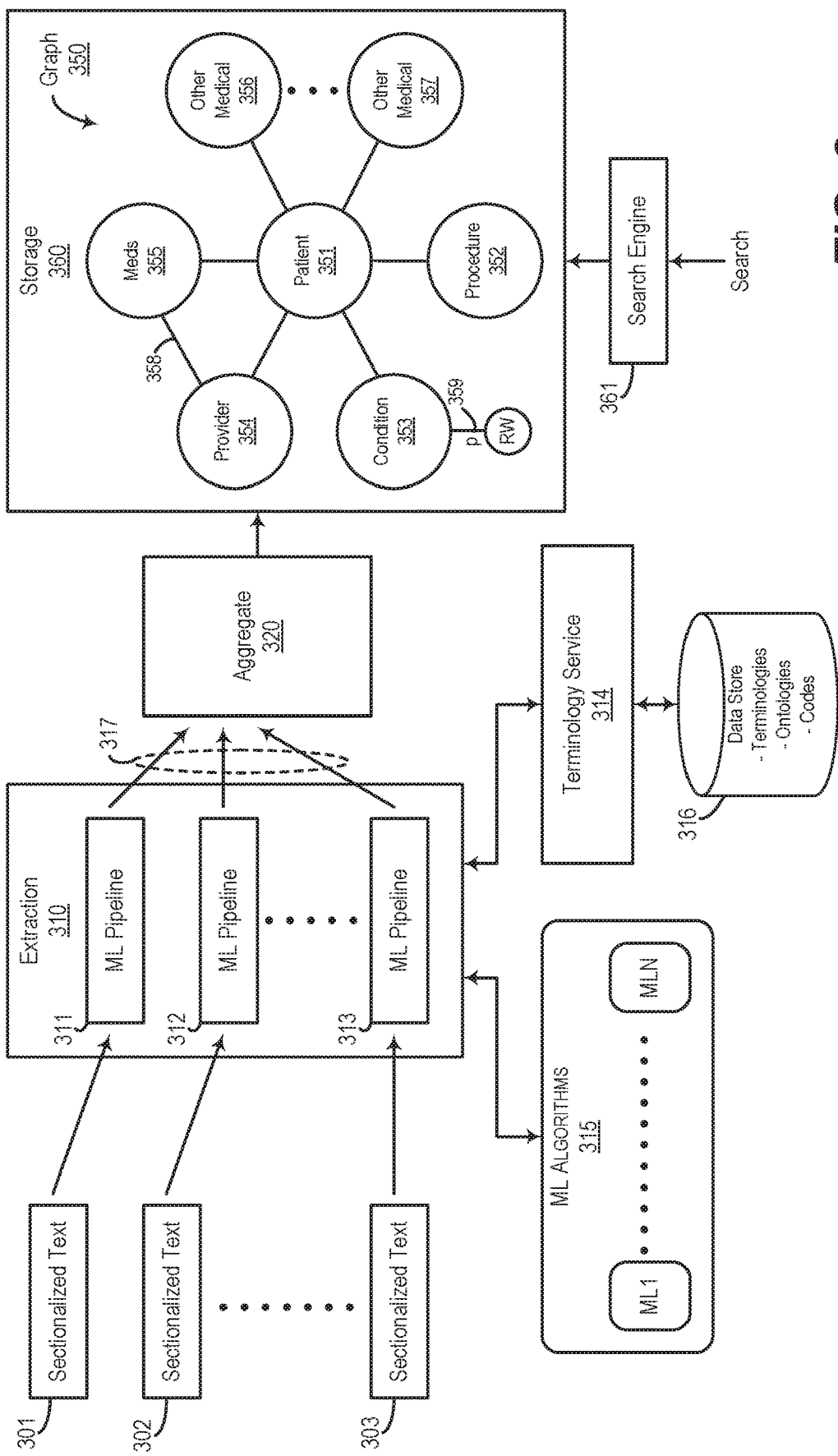
FIG. 3 illustrates generating and storing structured clinical data records according to an embodiment.

FIG. 3 illustrates generating and storing structured clinical data records according to an embodiment. In this example, sectionalized text is input to a plurality of ML pipelines in an extraction service 310. For example, text 301 associated with sections having a first classification may be classified using a first set of NLP algorithms from ML algorithms 315 using ML pipeline 311, text 302 associated with sections having a second classification may be classified using a second set of NLP algorithms from ML algorithms 315 using ML pipeline 312, and text 303 associated with sections having a yet another classification may be classified using a another set of NLP algorithms from ML algorithms 315 using ML pipeline 313, for example. In various embodiments, ML algorithms selected for the pipelines may comprise one or more of the following: a clinical entity NLP algorithm, a cancer entity NLP algorithm, a demographic entity NLP algorithm, a demographic ML model, a provider entity NLP algorithm, and a provider ML model. The clinical entity NLP algorithm may recognize clinical entities such as one or more of: medications, conditions, labs, procedures, diagnosis, vitals, allergies, treatments, and genomic alterations, for example.

As mentioned above, an extraction component 310 may transform text associated with the sections into a plurality of structured clinical data records, where different combinations of classified words or phrases of the text for different sections are mapped to structured clinical data records. In one embodiment, mapping combinations of classified words or phrases of text may include sending the classified words or phrases of text for each particular section to a terminology service 314 to determine medical codes, for example. Terminology service 314 may match the recognized entities (e.g., a classified word or phrase) to terminologies/codes stored in data store 316, for example.

The outputs of the pipelines 311-313 are structured clinical data records 317 (e.g., clinical statements as described below). In one embodiment, structured clinical data records 317 may comprise one or more medical codes retrieved from data store 316 based on one or more classifications of the words or phrases of the text, for example, and the medical codes are associated with one or more of the words or phrases of the text. Example structured clinical data records (e.g., clinical statements) are shown below.

The following is a list of example ML algorithms 315 that may be used in one or more of the ML pipelines 311-313 for classifying words or phrases in the text:

Clinical Entity Recognizer (NLP) (recognizes Medications, Labs, Procedures, Diagnosis, Vitals, Immunizations, Allergies, Genomic Alterations etc.)

Cancer Entity Recognizer (NLP)—For cancer specific entities like Stage, Performance, Disease status etc.

Demographic Entity Recognizer (NLP, ML Model)

Provider Entity Recognizer (NLP, ML Model)

Shape Recognizer (ML Model)—recognizes dates, phone numbers, MRN etc.

From the above list and from the list presented for the sectionalizer above, it can be seen that in some embodiments one or more NLP algorithms for recognizing clinical entities may be used both (1) as the ML algorithms for analyzing the body portions of sections/subsections and verifying certain section/subsection classifications and (2) as the ML algorithms used in the ML pipelines 311-313 for extraction, for example, which advantageously allows fewer ML algorithms to be required to complete the processing steps.

In this example, structured clinical data records 317 are input to an aggregator 320. Aggregator 320 may perform a number of functions are part of storing the data records in a searchable data structure, including the following: create record, merge attributes, insert, update, de-duplicate, add synonyms, add documents, and add key values to name just a few operations.

In this example, the searchable data structure is a graph data structure 350 comprising a plurality of nodes and edges between the nodes. For example, graph data structure may include nodes 351-357 corresponding to one or more of: a patient, a procedure, a condition, a provider, a medication, and a variety of other medically relevant entities. Each of the nodes may represent one or more entities. In one embodiment, different entities may be stored in different instances of nodes. For example, a medication node 355 may store data about a particular medication, and a patient may be connected to multiple medication nodes 355 corresponding to different medications, for example. Similarly, a provider node 354 may store data about a particular health care provider (e.g., a particular doctor, hospital, or other entity), and a patient may be connected to multiple provider nodes 354 corresponding to different providers the patient has seen. One or more provider nodes 354 may be connected to a medication node 355 if the provider prescribed a medication, for example. Similarly, a patient node 351 may be connected to one or more condition nodes 353, procedure nodes 352, or various other clinical nodes 356-357, for example. Additionally, in some embodiments, particular nodes may be coupled to other patients (not shown). For example, a provider node 354 may be coupled to many patient nodes. Condition nodes 353, procedure nodes 352, medication nodes 355, and other nodes may similarly be connected to multiple different patient nodes 351, for example.

As mentioned above, different nodes store data associated with each particular node. For example, patient nodes may include information about a particular patient (e.g., age, height, weight, etc. . . . ). Different medication nodes 355 may store information about different medications. Procedure nodes may store information about procedures. Condition nodes may store information about conditions. Provider nodes may store information about providers. And so on for other types of nodes. Each node may be an instance of the node type and store data about one entity of that type.

In one example embodiment, each node stores temporal data. For example, a plurality of the nodes may store data and a date or time (or both) associated with the data. One or more nodes may store an exact date or time (e.g., the time of an office visit, observation, or diagnosis) or a temporal range (e.g., a date range that a patient was on particular medication or a time range during which a patient on a treadmill together with an observed heart beat). Storing temporal information may allow a user to conduct a search based on temporal terms, such as, for example, "all patients who have been off a particular chemotherapy drug for at least three (3) months," which may be a criteria for inclusion in a clinical trial as mentioned above. Such a search is currently extremely challenging. Embodiments of the present disclosure may allow such previously challenging searches to be done quickly and easily, for example.

In this example, the patient node is connected to all the other nodes. However, some nodes may not be connected to the patient node (e.g., a medication node 355 may not be connected to a patient if the patient is not now and/or has not ever been on any medications).

Nodes of the graph may be connected together by edges. In one embodiment, the edges describe a relationship between the nodes. For instance, in one example embodiment, an edge software construct may have an attribute describing a relationship between two nodes. In particular, an edge attribute may describe connection between a patient node and another node using a clinical concept or clinical domain of a plurality of predefined clinical concepts or clinical domains. For example, the attribute may specify that a patient "took" a medication, provider "prescribed" a medication, patient "uses" provider, patient "has" a condition, or patient "underwent" a procedure. It is to be understood that edges may have one or more of a wide number of attributes in various embodiments, for example.

Features and advantages of some embodiments includes storing data in a graph data structure comprises edges having at least one probability attribute. For example, an edge 359 between a node for red wine (RW) and a condition node for headaches may have an associated probability, p (e.g., red wine causes headaches 0.1% of the time). However, an analysis of the graph and connections between many patient nodes, headache condition nodes, and red wine nodes may indicate that there is a stronger correlation between red wine and headaches than 0.1%. Accordingly, an edge between nodes having a probability may be updated based on an analysis of the graph, for example.

As mentioned above, a user may search the graph by entering a search into a search engine 361. The temporal information stored in some embodiments may allow a user perform medical searches on a temporal basis (e.g., at particular times or across date ranges) and obtain results corresponding to snapshots or slices of the data stored in the graph at a particular time or over a particular time range, for example.

The following sections describe additional examples and embodiments of sectionalization and extraction according to various embodiments.

A. Sectionalization

Figure 4:
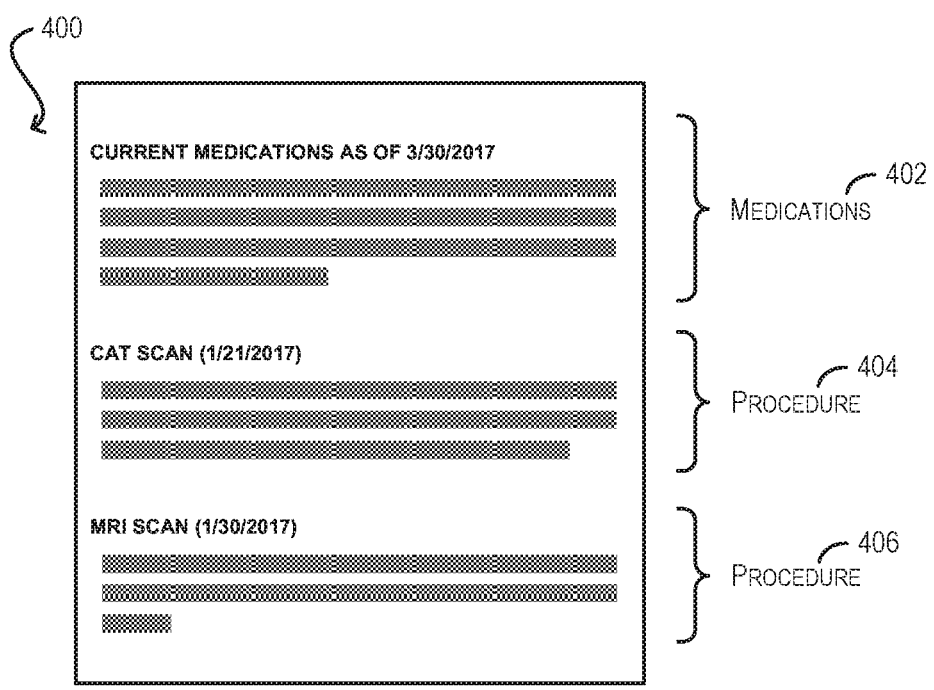
FIG. 4 illustrates an example clinical document that has been sectionalized according to an embodiment.

As noted previously, in various embodiments the sectionalization service of the present disclosure is responsible for partitioning each clinical document ingested by the platform into logically distinct portions, referred to sections. As part of this process, the sectionalization service can classify, with the help of a control component communicatively coupled with a plurality of ML algorithms and a terminology service, each determined section as corresponding to a particular clinical concept or clinical domain based on that section's content. By way of example, FIG. 4 depicts a clinical document 400 that has been partitioned—or in other words, sectionalized—into a medications section 402, a first procedure section 404, and a second procedure section 406. Upon completing this sectionalization task, the sectionalization service can pass the determined sections and their corresponding classifications to a downstream extraction service to facilitate further document processing.

Figure 5:
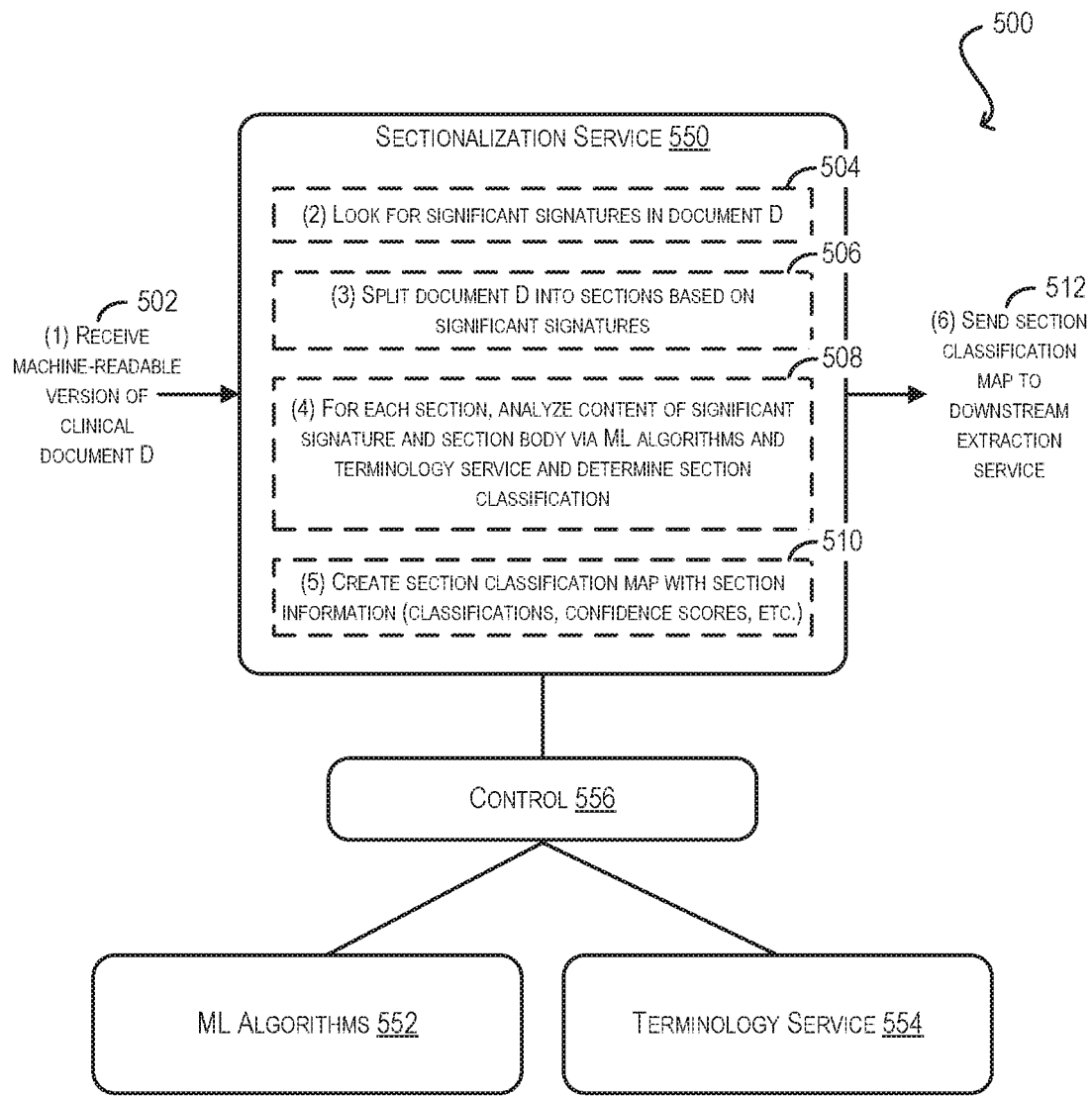
FIG. 5 illustrates a sectionalization service and high-level sectionalization workflow according to an embodiment.

FIG. 5 illustrates a high-level workflow 500 that may be executed by a sectionalization service 550 for sectionalizing a given clinical document D according to certain embodiments. At step (1) of FIG. 0.5 (reference numeral 502), sectionalization service 550 can receive a machine-readable version of clinical document D. In scenarios where clinical document D was originally ingested by the platform in a machine-readable format (e.g., a machine-readable PDF (Portable Document Format) document, an ASCII text document, etc.), that document may be provided directly to sectionalization service 550 at step (1). Alternatively, in scenarios where clinical document D was originally ingested by the platform in a non-machine-readable format (e.g., as one or more scanned images), document D can be converted into a machine-readable format via the platform's OCR service and the output of the OCR service can be passed to sectionalization service 550.

At step (2) (reference numeral 504), sectionalization service 550 can scan though the machine-readable version of clinical document D and look for certain text strings (referred to herein as "significant signatures") in the document content that appear to be section headers. In one set of embodiments, these significant signatures can be identified based on their text formatting properties such as font style, size, position, color, capitalization, and/or the like. For example, if sectionalization service 550 encounters a text string that is left-justified, capitalized, and uses a font size larger than its surrounding text, service 550 may conclude that this text string is a significant signature because it exhibits formatting characteristics that are commonly exhibited by header text. In other embodiments, the significant signatures can be identified via other means, such as via explicit structural metadata (e.g., HTML (Hyper Text Markup Language) or XML (Extensible Markup Language)-based header tags) included in the machine-readable version of clinical document D.

At step (3) (reference numeral 506), sectionalization service 550 can split the machine-readable version of clinical document D into sections based on the identified significant signatures. For instance, assume clinical document D is 200 lines long and a first significant signature is found at line 1, a second significant signature is found at line 78, and a third significant signature is found at line 152. In this case, sectionalization service 550 can split the document into a first section spanning from line 1 to line 77, a second section spanning from line 78 to line 151, and a third section spanning from line 152 to line 200.

Then, for each determined section, sectionalization service 550 can analyze, in cooperation with a control component 556 that is coupled with one or more ML algorithms 552 and a terminology service 554, the content of the significant signature (i.e., section header) and the section body in order to determine an appropriate classification for the section (step (4), reference numeral 508). In certain embodiments, the possible classifications for a given section can be selected from among a predefined list of common clinical concepts/domains, including one or more of the following:

Medications
Diagnosis
Procedure
Lab results
Gene report
Allergies
Vitals
Immunization
Demographics
Organization
Provider
Reason for Visit
History of Present Illness The specific processing that may be performed via control component 556, ML algorithms 552, and terminology service 554 to determine each section classification at step (4) is detailed in sub-section A.1 below.

Upon determining the section classifications for clinical document D, sectionalization service 550 can create a data structure (referred to herein as a "section classification map") that includes this classification information, along with other section-related metadata (e.g., mapping of each section to its corresponding document content, overall confidence score for each classification, contribution of the significant signature content to the confidence score, contribution of the section body content to the confidence score, etc.) at step (5) (reference numeral 510). For example, listing 1 below depicts a portion of an example section classification map with three section entries associated with classifications "medication," "procedure," and "diagnosis." Each section entry includes a "probability" field indicating an overall confidence score or likelihood that the section classification is correct (as determined by via control component 556.ML algorithms 552) as well as "section_heading" and "section_body" fields indicating the likelihood that the classification is correct based on the content in those portions respectively.

{
   "medication": {

```
    "probability": "68":
    "section_heading": "88",
    "section_body": "54",
  }
  "procedure": {
    "probability": "90":
    "section_heading": "95",
    "section_body": "87",
  }
  "diagnosis": {
    "probability": "74":
    "section_heading": "70",
    "section_body": "75",
  }
}
```

Listing 1

Finally, at step (6) of FIG. 5 (reference numeral 512), sectionalization service 550 can pass the section classification map for clinical document D to a downstream extraction service to perform per-section entity/statement extraction. Further, although not shown, workflow 500 optionally can return to step (1) in order to process additional incoming clinical documents.

With the high-level sectionalization approach shown in FIG. 5 and described above, a number of benefits are realized. First, because this approach breaks down a clinical document into logically distinct sections that each pertain to a specific clinical concept or domain (e.g., medications, diagnosis, procedures, etc.), the downstream extraction service can analyze and extract clinical entity and statement information from each section in a focused manner based on the section's classification. For instance, if a first section S1 is classified as pertaining to medications, the extraction service can identify and extract entities/statements from section S1 using ML algorithms/techniques that are specifically tailored to the medications domain. Similarly, if second section S2 is classified as pertaining to a procedure, the extraction service can identify and extract entities/statements from section S2 using ML algorithms/techniques that are specifically tailored to the procedures domain. Thus, sectionalization enables the extraction service to perform its functions in a more accurate and efficient manner.

Second, by splitting a clinical document into smaller, more manageable portions for downstream components, sectionalization facilitates the processing of very large clinical documents. In certain embodiments (described in sub-section A.2 below), sectionalization service 550 can implement a slightly modified version of the sectionalization workflow shown in FIG. 5 that operates on a page-by-page basis, which in turn allows sectionalization service 550 to easily and efficiently sectionalize clinical documents of any page length.

A.1 Determination of Section Classifications Via NLP

Figure 6:
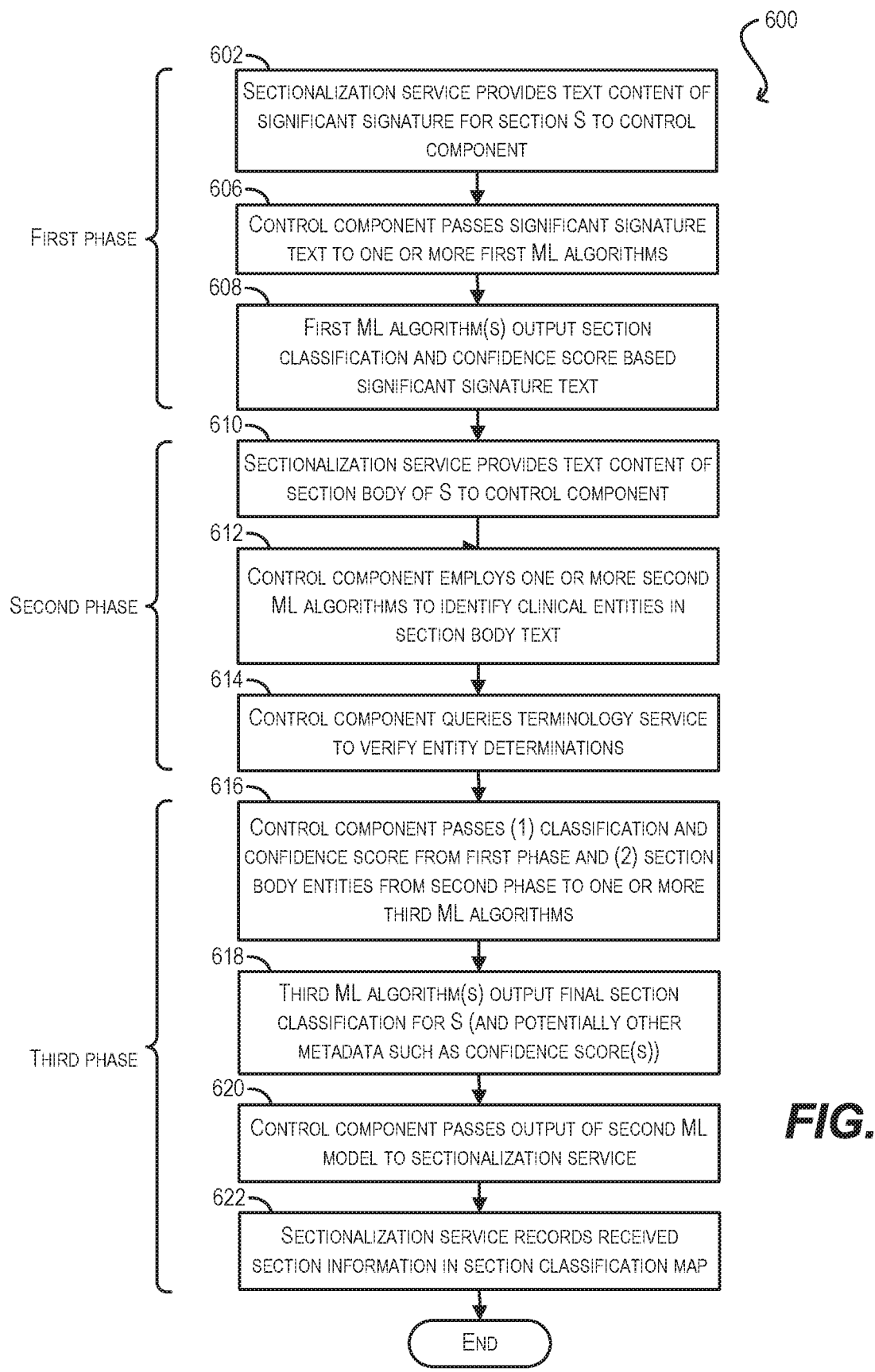
FIG. 6 illustrates a flowchart with additional details regarding the sectionalization workflow of FIG. 5 according to an embodiment.

FIG. 6 is a flowchart 600 that details the processing that may be performed by sectionalization service 550, control component 556, ML algorithms 552, and terminology service 554 for determining a classification for a given section S of a clinical document (per step (4) of high-level workflow 500) according to certain embodiments. Generally speaking, flowchart 600 proceeds according to three phases: (1) a first phase that involves analyzing the significant signature indicating the start of section S; (2) a second phase that involves analyzing the body of section S; and (3) a third phase that involves determining a final section classification for S based on the outcomes of the first and second phases.

Starting with the first phase (significant signature analysis), at block 602 sectionalization service 550 can provide the text content of the significant signature associated with section S to control component 556. In response, control component 556 can pass the significant signature text to one or more first ML algorithms 552, which are trained to classify the text as corresponding to one of the clinical section classifications discussed earlier (block 606). In response, at block 608, the first ML algorithm(s) can output a likely section classification, along with a confidence score, based on the provided significant signature text. For instance, returning to the example above, if the phrase "current medications" is provided as input to the first ML algorithm(s), they may output the section classification "medications" and a confidence score of "78." In this case, a confidence score of 78 indicates that the first ML algorithm(s) are reasonably confident that "medications' is the correct classification for a clinical document section having the words "current medications" in its section header.

Once the first ML algorithm(s) have output its section classification and confidence score for the significant signature text per block 608, control component 556 can save these results and the first phase can end.

Turning now to the second phase (section body analysis), at block 610 sectionalization service 550 can provide the text content of the body of section S (i.e., the span of content from the significant signature of S to the next significant signature in the document) to control component 556. In response, control component 556 can employ one or more second ML algorithms (comprising, e.g., a NER algorithm) to process this section body text and identify all of the known clinical entities that appear in that text (block 612). For example, if the section body text includes the sentence "Dexamethasone started with improvement in symptoms but continued cognitive difficulty," the NER algorithm may identify the word "Dexamethasone" as corresponding to a "drug" entity, the word "improvement" as corresponding to a "course" entity, and the phrase "continued cognitive difficulty" as corresponding to a "problem" entity.

As part of this entity identification process, in certain embodiments control component 556 may query terminology service 554 to validate one or more entity determinations made by the NER algorithm (block 614). For instance, if the NER algorithm determines that "Dexamethasone" is a "drug" entity, control component 556 may ask terminology service 554 to search for "Dexamethasone" in its available drug/medicine databases. If terminology service 554 indicates that the word is found, control component 556 can have heightened confidence that the entity determination is correct. On the other hand, if terminology service 554 indicates that the word was not found, control component 556 may delete or otherwise disregard the entity determination.

It should be noted that in some cases, the section body for a given section may include sub-sections. In these cases, the body of each sub-section may be analyzed and entities in those sub-section bodies may be identified per blocks 612 and 614.

Once control component 556 has identified all of the clinical entities in the body of section S via the second ML algorithm(s), the second phase can end and the third phase (classification determination) can begin. In particular, at block 616, control component 556 can take (1) the section classification and confidence score determined via the first phase at block 608 and (2) the section body entities identified via the second phase at blocks 612/614 and provide both (1) and (2) as inputs to one or more third ML algorithm(s).

In response, the third ML algorithm(s) can generate a final section classification for section S (and a confidence score for that final classification) based on all of these inputs (block 618). For example, the third ML algorithm(s) may output a final section classification of "medications" with a confidence score of "95," indicating that this is highly likely to be the correct classification for section S.

In certain embodiments, as part of its training, the third ML algorithm(s) may be tuned to place different weights on the first phase and second phase inputs in order to arrive at the final section classification. For instance, the third ML algorithm(s) may be trained to weigh the section classification determined at block 608 at 20% and weigh the section body entities determined at blocks 612/614 at 80%. Further, in addition to outputting a final section classification and final confidence score at block 618, the third ML algorithm (s) may also output a separate confidence score for each of the first and second phase inputs, which provides an indication of their respective contributions to the final classification result.

Finally, at blocks 620 and 622, control component 556 can pass the final section classification and related information (e.g., confidence scores(s)) to sectionalization service 550, which can record this information in its section classification map. Flowchart 600 can subsequently end.

It should be appreciated that flowchart 600 is illustrative and various modifications are possible. For example, although flowchart 600 presents the first, second, and third phases as occurring in a particular sequential order, in other embodiments one or more of these phases may be performed in parallel or in a different order. For instance, in a particular embodiment control component 556 may execute the first phase (significant signature analysis) and the second phase (section body analysis) concurrently.

Further, although flowchart 600 assumes that section S has an associated significant signature, in some scenarios this may not be the case. For instance, consider a scenario where a clinical document is scanned for significant signatures and the first signature is not found until some point midway through the document. In this case, the section spanning from the start of the document to the first significant signature will not have an associated signature of its own. For this and other similar situations, control component 556 can perform section classification based solely on the content of the section body (phases 2 and 3) and thus omit the significant signature analysis (phase 1).

Yet further, although not shown in FIG. 6, in certain embodiments control component 556 can take into account non-textual content included in a given section as part of its classification determination processing. For example, assume section S includes a medical image (e.g., body scan, x-ray, etc.). In this case, control component 556 can invoke a computer vision component of the platform to determine the content of the image, determine, via its NER algorithm, a clinical entity associated with the image description, and then provide that entity information as another input into the third ML algorithm(s).

A.2 Page-Based Sectionalization

Figure 7:
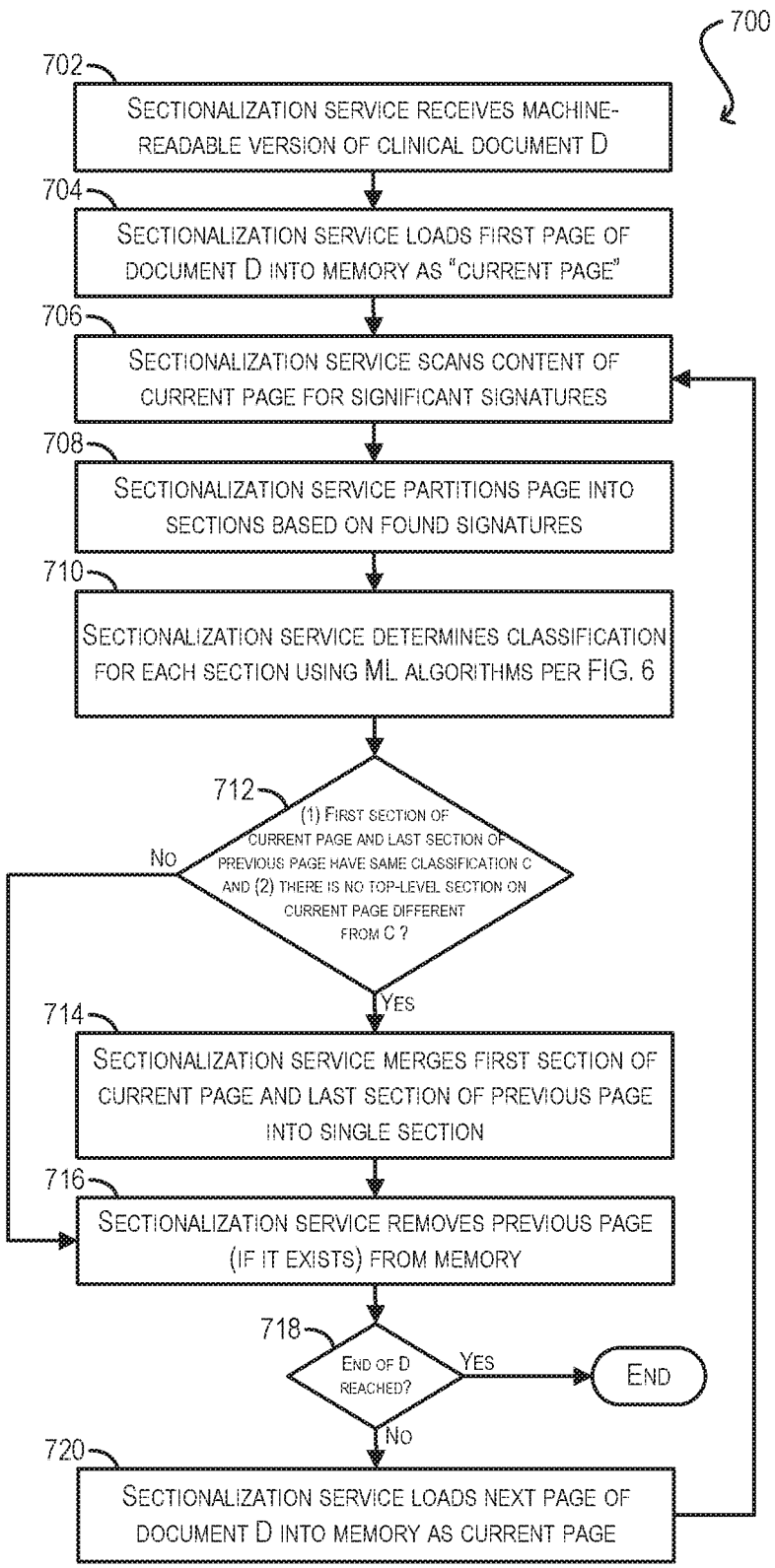
FIG. 7 illustrates a flowchart for performing page-based sectionalization according to an embodiment.

In certain embodiments, in lieu of the general sectionalization approach shown in FIG. 5, sectionalization service 550 can implement a page-based sectionalization approach that specifically partitions a clinical document on a page-by-page basis. One advantage of this approach is that it allows sectionalization service 550 to operate on the document in page-sized chunks and thus does not require the entirety of the document to be loaded into system memory at once (which can be problematic for very large documents). FIG. 7 depicts a flowchart 700 of this page-based sectionalization approach according to certain embodiments.

Starting with blocks 702 and 704, sectionalization service 550 can receive a machine-readable version of a clinical document D and can load the first page of the document into memory. Sectionalization service 550 can then scan the content of this current in-memory page for significant signatures (block 706), partition the page into sections based on the found signatures (block 708), and determine a classification for each section using the processing described in FIG. 6 above (block 710).

Once the classifications for the current page's sections have been determined, sectionalization service 550 can check whether (1) the first section for the current page and the last section of the previous page (if such a previous page exists) have the same classification C, and (2) there is no top-level section at the start of the current page that is different from C (block 712). If the answer is yes, sectionalization service 550 can merge those two sections into a single section (block 714). Sectionalization service 550 can then remove the previous page (if it exists) from memory (block 716) and check whether the end of clinical document D has been reached (i.e., whether the current page is the last page in the document) (block 718).

If the end of the document has been reached, flowchart 700 can end. Otherwise, sectionalization service 550 can load the next page in document D into memory (block 720). Finally, flowchart 700 can loop back to block 706 in order to sectionalize this next page, and the process can repeat until the entire document is processed.

Figure 8:
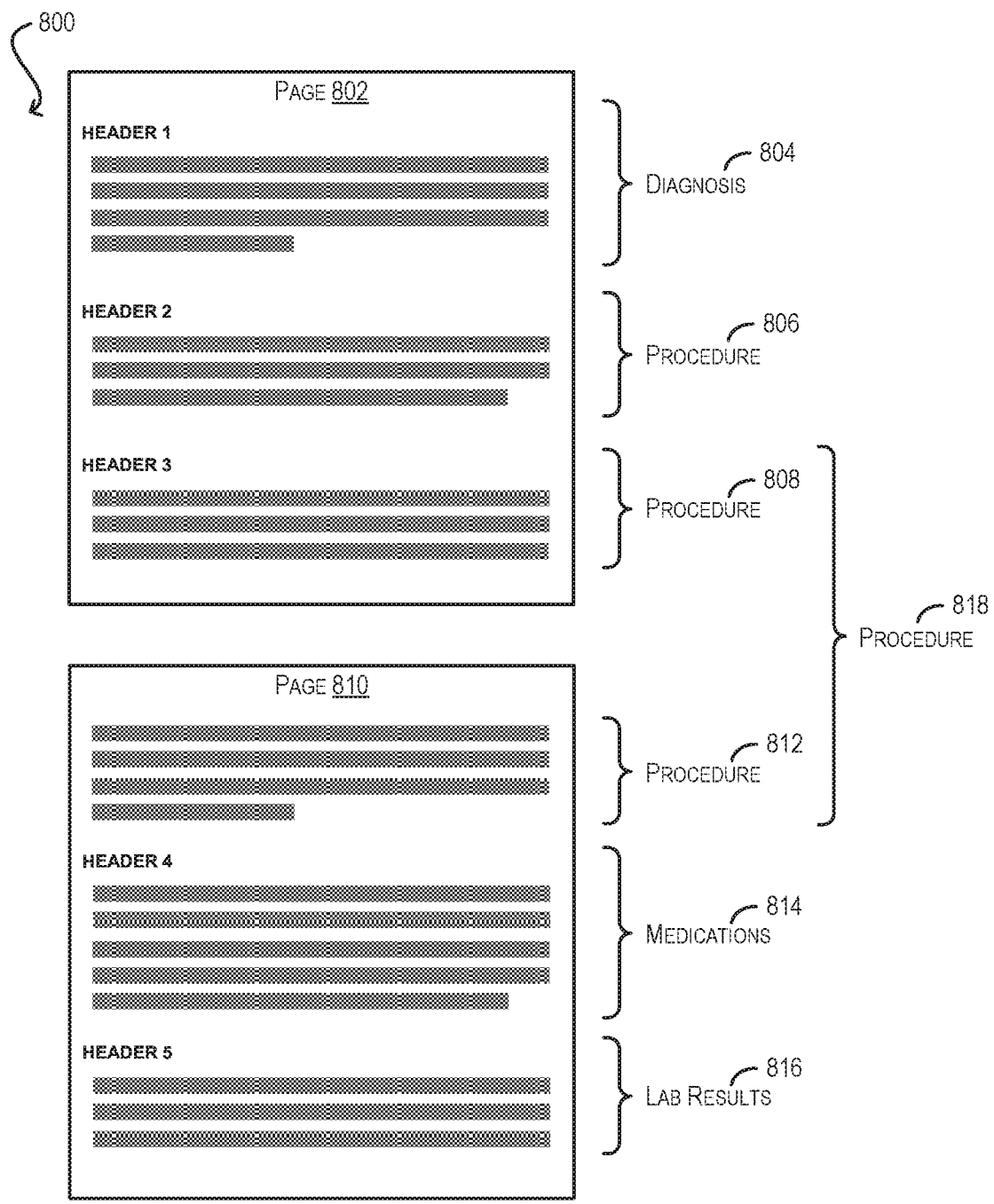
FIG. 8 illustrates an example clinical document that has been sectionalized using the page-based approach of FIG. 7 according to an embodiment.

To illustrate the foregoing, FIG. 8 depicts an example clinical document 800 that has been sectionalized using the page-based approach of FIG. 7. As shown in FIG. 8, document 800 includes a first page 802 that is initially sectionalized into three sections 804, 806, 808 and second page 810 that is initially sectionalized into three sections 812, 814, and 816. The last section 808 of first page 802 is subsequently merged with the first section 812 of second page 810 per block 716 of FIG. 7 into a single section 818 because sections 808 and 812 have the same classification ("Procedure") and there is no intervening significant signature/header between them.

B. Entity Extraction

As mentioned above, an extraction block may be configured to extract clinical entities from sections of clinical documents partitioned by sectionalization block. In some embodiments, the sectionalization and extraction blocks services. As part of the extraction process, an extraction service can analyze a particular section of a clinical document and identify, with the help of entity recognizer ML algorithms entities in the particular section. An extraction service may then generate clinical statements that represent clinical entities based on the identified entities in the particular section. For each clinical statement, the extraction service can determine, with the help of a terminology service, codes for the clinical statement and associate the codes with the clinical statement. The codes associated with the clinical statements allow for downstream components to further process the clinical statements. Once an extraction service completes the clinical entity extraction process for the particular section of the clinical document, the extraction service can pass the clinical statements representing the clinical entities to an aggregator block (or aggregation service) for further clinical entity/statement processing. The extraction service may then continue processing any remaining unprocessed sections in the clinical document.

In some embodiments, a clinical entity may be one of the clinical concepts/domains in the predefined list of common clinical concepts/domains mentioned above (e.g., a medication, a diagnosis, a procedure, a lab result, a gene report, an allergy, a vital, an immunization, an organization, a provider, etc.). A clinical entity may also be one of other clinical concepts/domains such as a genetic mutation, a patient, etc.

Figure 9:
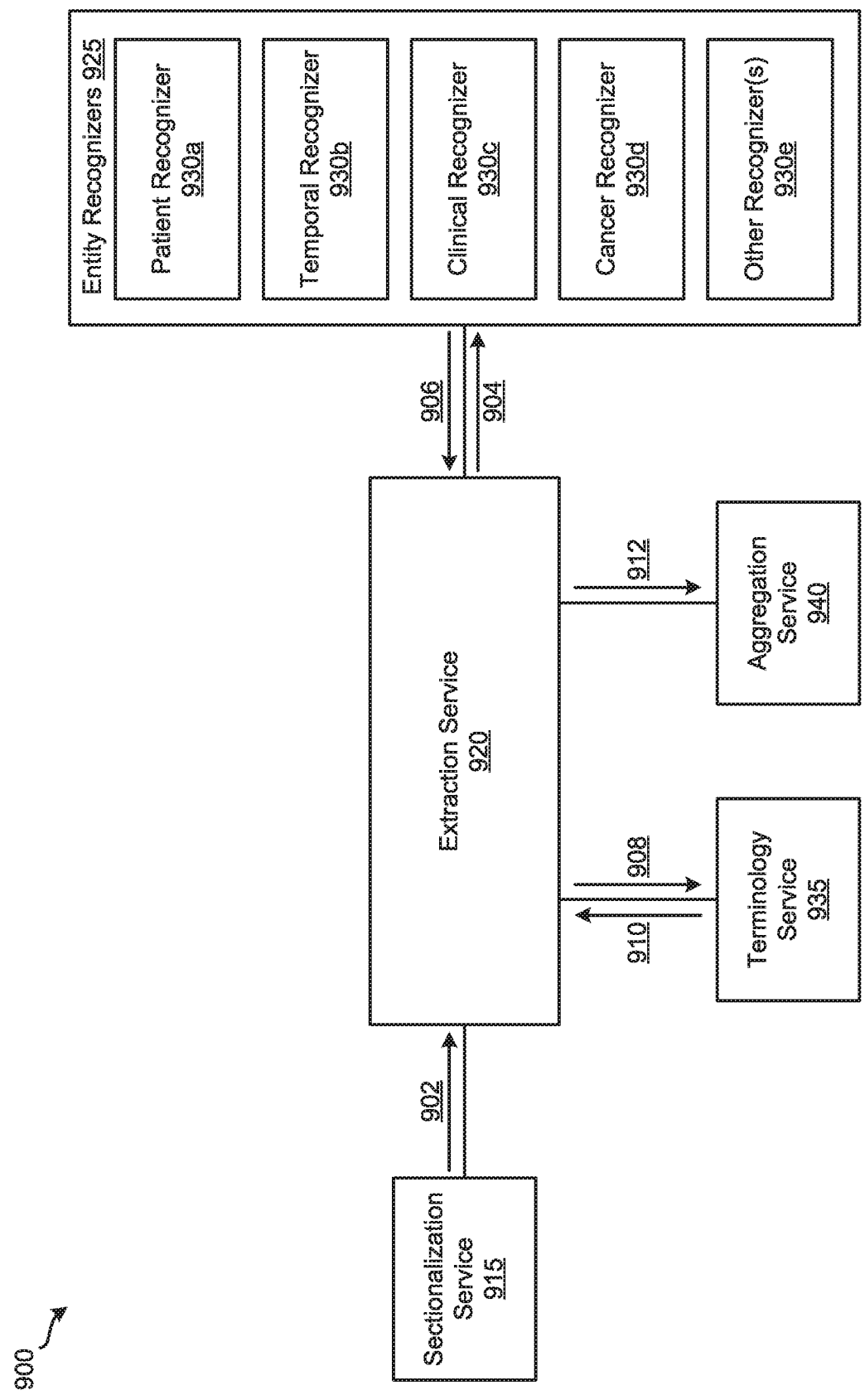
FIG. 9 illustrates an example data flow through a system for extracting entities from a section of a clinical document according to an embodiment.

FIG. 9 illustrates an example data flow through a system 900 for extracting entities from a section of a clinical document according to some embodiments. Before describing data flow, components of system 900 will be described. As shown, system 900 includes sectionalization service 915, extraction service 920, entity recognizers 925, terminology service 935, and aggregation service 940. In some embodiments, sectionalization service 550 or sectionalization block 111 may be used to implement sectionalization service 915; ML algorithms 115 can be used to implement entity recognizers 925; terminology service 554 or terminology service 314 can be used to implement terminology service 935; and aggregation block 320 may be used to implement aggregation service 940.

Sectionalization service 915 is configured to partition clinical documents into sections and classify the sections in a similar manner as described above. Once sectionalization service 915 has partitioned a clinical document into sections and classified the sections, sectionalization service 915 may send the partitioned clinical document and the classification of the sections to extraction service 920.

Extraction service 920 is responsible for extracting entities from sections of clinical documents. For example, when extraction service 920 receives from sectionalization service a partitioned clinical document and classifications for the portioned sections for the clinical document, extraction service 920 may extract, with the help of entity recognizers 925 and terminology service 935, clinical entities from the clinical document on a section-by-section basis.

As illustrated in FIG. 9, entity recognizers 925 includes patient recognizer 930a, temporal recognizer 930b, clinical recognizer 930c, cancer recognizer 930d, and other recognizer(s) 930e. Each entity recognizer 925 is configured to analyze a given text (e.g., a section of a clinical document) and, based on the analysis, identify terms and/or groups of terms in the given text as being data associated with a particular type of data. For example, patient recognizer 930a is configured to identify terms and/or groups of terms as being data associated with patient data (e.g., first name, last name, middle name, date of birth, etc.). Temporal recognizer 930b may be configured to identify terms and/or groups of terms as being data associated with temporal data (e.g., dates, times, etc.). In some embodiments, patient recognizer 930a and temporal recognizer 930b use machine learning (ML) techniques/algorithms to identify their respective types of entities. In some such embodiments, an ML model trained to identify patient data is employed by patient recognizer 930a and an ML model trained to identify temporal data is used by temporal recognizer 930b. Clinical recognizer 930c may be configured to identify terms and/or groups of terms as being data associated with clinical data. In some embodiments, clinical data is data associated with or based on observation and/or treatment of a disease in a patient. Cancer recognizer 930d can be configured to identify terms and/or groups of terms as being data associated with cancer data. In some embodiments, clinical recognizer 930c and cancer recognizer 930d use NLP techniques/algorithms to identify their respective types of data. In some such embodiments, the NLP techniques/algorithms used by clinical recognizer 930c include a bag-of-words approach and/or an NLP model trained to identify terms and/or groups of terms as being data associated with clinical data and the NLP techniques/algorithms used by cancer recognizer 930d include a bag-of-words approach and/or an NLP model trained to identify terms and/or groups of terms as being data associated with clinical data.

Other recognizer(s) 930e may be configured to identify terms and/or groups of terms as being data associated with other types of data. Other recognizer(s) 930e can use ML techniques/algorithms, NLP techniques/algorithms, or a combination thereof to identify terms and/or groups of terms as being data associated with other types of data. Other recognizer(s) 930e is shown as one recognizer in FIG. 9 for the purposes of simplicity and explanation. One of ordinary skill in the art will understand that any number of additional and/or different recognizers configured to identify terms and/or groups of terms as being data associated with different types of data may be utilized in different embodiments. For instance, entity recognizers 925 may include a recognizer configured to identify terms and/or groups of terms as being data associated with organization data (e.g., hospitals, medical groups, clinics, medical universities, medical specialists' offices, nursing homes, laboratories, rehabilitation facilities, etc.), a recognizer configured to identify terms and/or groups of terms as being data associated with provider data (e.g., physician name, physician identifier (ID), etc.).

Terminology service 935 is responsible for validating the identification, by entity recognizers 930a-e, of terms and/or groups of terms as being data associated with certain types of data. Additionally, terminology service 935 handles the determination of medical codes for terms and/or groups of terms. For both of these operations, terminology service 935 may leverage a number of different data stores that each store medical codes that represent different types of medical concepts. Examples of such data stores include an RxNorm data store for medications, a Logical Observation Identifier Names and Codes (LOINC) data store for labs, a Current Procedural Terminology (CPT) data store for procedures, and a ICD-10-CM (International Classification of Diseases, Tenth Revision, Clinical Modification) data store for diagnoses.

Aggregation service 940 is configured to manage clinical statements. For instance, when aggregation service 940 receives a clinical statement from extraction service 920, aggregation service 940 can perform a variety of different operations. If aggregation service 940 determines that a clinical statement is unique, aggregation service 940 may add it to a data store configured to store clinical statements. If aggregation service 940 determines that a clinical statement is a duplicate of an existing clinical statement, aggregation service 940 can delete it. Upon determining that a received clinical statement and another clinical statement managed by aggregation service 940 represent the same clinical entity but the received clinical statement and other clinical statement managed by aggregation service 940 are not the same, aggregation service 940 may merge the data of the received clinical statement with the other clinical statement managed by aggregation service 940.

The example data flow through system 900 begins by extraction service 920, at 902, receiving from sectionalization service 915 a clinical document and a section classification map for the clinical document. Upon receiving these items from sectionalization service 915, extraction service 920 can identify a section in the clinical document based on the section classification map. Next, extraction service 920 sends, at 904, the section to a set of entity recognizers 925 for processing. Extraction service 920 may send the section to a particular set of entity recognizers 930 for processing based on the classification of the section. For instance, extraction service 920 may send the section to patient recognizer 930a if the section is classified as a demographics section. For provider sections, extraction service 920 sends the sections to a recognizer (e.g., recognizer 930e) that is configured to identify terms and/or groups of terms as being data associated with provider data. If the section is classified as an organization section, extraction service may send the section to a recognizer (e.g., recognizer 930e) that is configured to identify terms and/or groups of terms as being data associated with organization data. For medicine sections, extraction service 920 can send the section to temporal recognizer 930b and clinical recognizer 930c. Extraction service 920 can send the section to temporal recognizer 930b, clinical recognizer 930c, and cancer recognizer 930d if the section is classified as a reason for visit section, a history of present illness section, a lab result section, a procedure section, a gene report section, an allergy section, a vitals section, an immunization section, or a diagnosis section.

When each entity recognizer 925 in the set of entity recognizers 925 receives the section from extraction service 920, it parses through the section, identifies terms and/or groups of terms in the section as being data associated with the types of data that the entity recognizer 930 is configured to identify, marks the identified terms and/or groups of terms, and then sends, at 906, the section back to extraction service 920. Upon receiving the section back from the set of entity recognizers 925, extraction service 920 sends, at 908, the section to terminology service 935 for further processing.

Once terminology service 935 receives the section, terminology service 935 validates, with the use of the data stores configured to store medical codes mentioned above, the identifications of terms and/or groups of terms in the section by the set of entity recognizers 930 as being data associated with certain types of data. Additionally, terminology service 935 determines medical codes for each of the validated terms and/or groups of terms and associates them with respective terms and/or groups of terms. In some embodiments, terminology service 935 determines the medical codes from the different data stores configured to store medical codes described above. After terminology service 935 finishes processing the section, terminology service 935 sends, at 910, the section back to extraction service 920. Then, extraction service 920 generates a clinical statement based on the validated and codified section. Finally, extraction service 920 send, at 912, the clinical statement to aggregation service 940 for further statement processing. Extraction service 920 may then continue processing any remaining unprocessed sections in the clinical document in the same or similar manner described above.

The example data flow explained above by reference to FIG. 9 describes how extraction service 920 can send a section of a clinical document to a particular set of entity recognizers 930 for processing based on the classification of the section. In some embodiments, extraction service 920 may utilize several different sets of entity recognizers 930 to identify terms and/or groups of terms in a section of a clinical document that are associated with different types of data. A set of entity recognizers 930 used to identify terms and/or groups of terms as being data associated with certain types of data may be referred to as an NLP pipeline. An NLP pipeline may be configured to perform other functions besides identify terms and/or groups of terms as being data associated with certain types of data. For instance, an NLP pipeline may be configured to classify a clinical document based on terms and/or groups of terms in a section of the clinical document. Extraction service 920 can use different sets of NLP pipelines to process a section of a clinical document based on the classification of the section (which is determined by sectionalization service 550).

Figure 10:
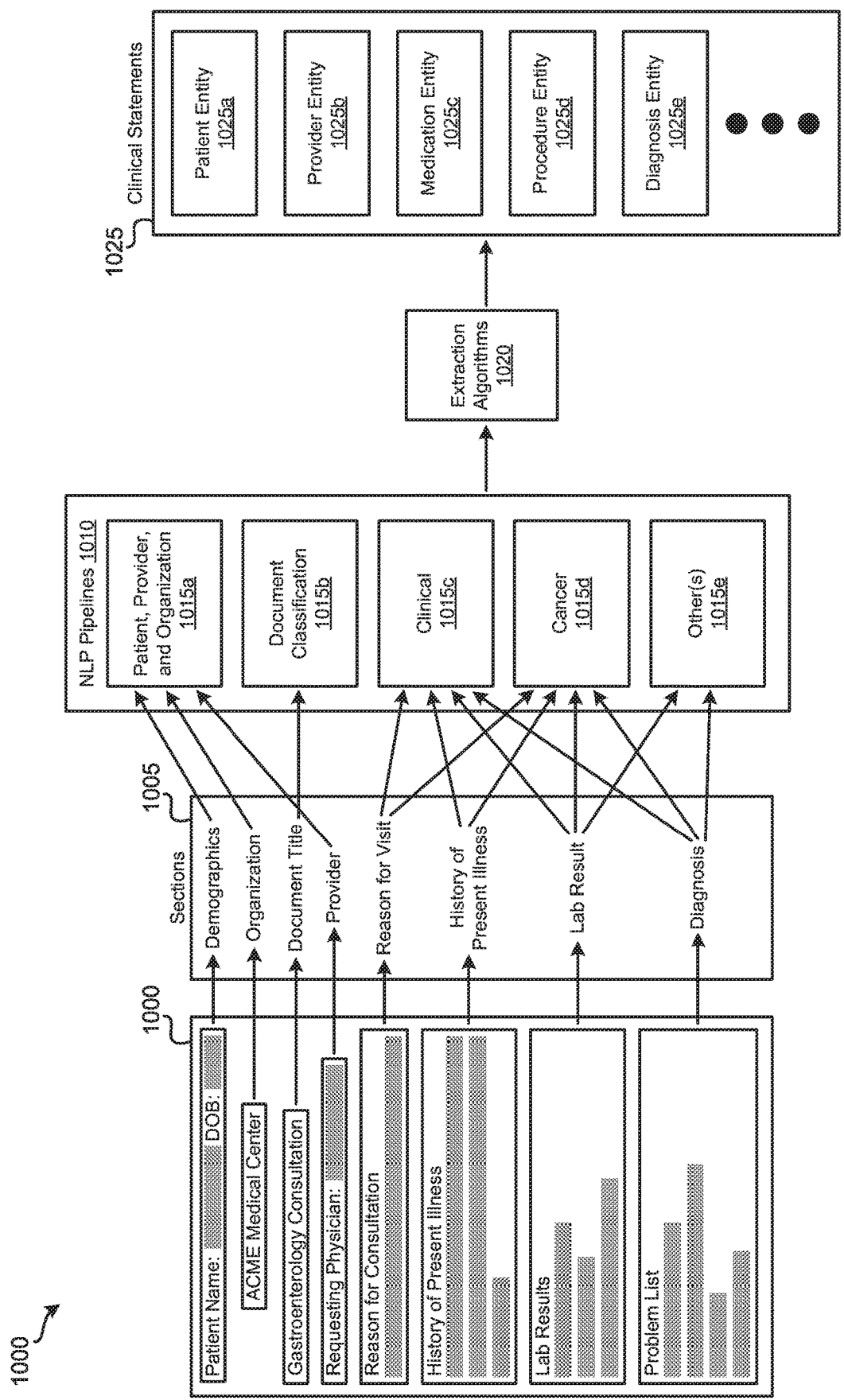
FIG. 10 illustrates an example of using different sets of NLP pipelines to process a section of a clinical document according to an embodiment.

FIG. 10 illustrates an example of using different sets of NLP pipelines to process a section of a clinical document according to some embodiments. As shown, FIG. 10 includes clinical document 1000, section classification map 1005, NLP pipelines 1010, extraction service 920, and clinical statements 1020. Clinical document 1000 includes eight sections, which have been partitioned and classified by sectionalization service 550. As indicated by section classification map 1005, which was generated by sectionalization service 550, the first section of clinical document 1000 has been classified as a demographics section, the second section of clinical document 1000 has been classified as an organization section, the third section of clinical document 1000 has been classified as a document title section, the fourth section of clinical document 1000 has been classified as a provider section, the fifth section of clinical document 1000 has been classified as a reason for visit section, the sixth section of clinical document 1000 has been classified as a history of present illness section, the seventh section of clinical document 1000 has been classified as a lab result section, and the eighth section of clinical document 1000 has been classified as a diagnosis section.

As shown, NLP pipelines 1010 includes patient, provider, and organization pipeline 1015a, document classification pipeline 1015b, clinical pipeline 1015c, cancer pipeline 1015d, and other pipelines 1015e. Each of the NLP pipelines 1015a-e can be implemented by one or more entity recognizers 930a-e. Patient, provider, and organization pipeline 1015a, which is configured to identify terms and/or groups of terms in a given text (e.g., a section of clinical document 1000) as being data associated with patient data, provider data, and/or organization data, may be implemented by patient recognizer 930a and other recognizer(s) 930e. Document classification pipeline 1015b, which is configured to classify a clinical document based on terms and/or groups of terms in a given text (e.g., a section of clinical document 1000), can be implemented by other recognizer(s) 930e. Clinical pipeline 1015c, which is configured to identify terms and/or groups of terms in a given text (e.g., a section of clinical document 1000) as being data associated with clinical data, may be implemented by temporal recognizer 930b, clinical recognizer 930c, and cancer recognizer 930d. Cancer pipeline 1015d, which is configured to identify terms and/or groups of terms in a given text (e.g., a section of clinical document 1000) as being data associated with cancer data, may be implemented by temporal recognizer 930b, clinical recognizer 930c, and cancer recognizer 930d. Other pipelines 1015e, which is configured to identify terms and/or groups of terms in a given text (e.g., a section of clinical document 1000) as being data associated with other types of data, may be implemented by any number of different combinations of entity recognizers 930a-e.

Once extraction service 920 receives clinical document 1000 and section classification map 1005 from sectionalization service 550, extraction service 920 can start processing clinical document 1000 on a section-by-section basis. FIG. 10 conceptually illustrates how extraction service 920 may send different sections of clinical document to different sets of NLP pipelines. As shown, extraction service 920 sends the demographics section, the organization section, and the provider section to patient, provider, and organization NLP pipeline 1015a. Extraction service 920 sends the document title section of clinical document 1000 to document classification NLP pipeline 1015b. In this example, extraction service 920 sends the reason for visit section and the history of present illness section to clinical NLP pipeline 1015c and cancer NLP pipeline 1015d. In addition, extraction service 920 sends the lab result section and the diagnosis section to clinical NLP pipeline 1015c, cancer NLP pipeline 1015d, and other(s) NLP pipeline 1015e.

By using one or more NLP pipelines 1015a-e and terminology service 935 (not shown in FIG. 10) to process a section of clinical document 1000, extraction service 920 can extract a set of clinical entities from the section based on the identified terms and/or groups of terms in the section. In some embodiments, extraction service 920 extracts a clinical entity from a section of a clinical document by generating a data structure (referred to as a clinical statement) representing the clinical entity. FIG. 10 also conceptually illustrates how extraction service 920 may generate clinical statements representing different types of clinical entities extracted from sections of a clinical document. As shown, clinical statements 1025 includes, among many other clinical statements representing a vast number of different types of clinical entities, a clinical statement representing a patient entity 1025a, a clinical statement representing a provider entity 1025b, a clinical statement representing a medication entity 1025c, a clinical statement representing a procedure entity 1025d, and a clinical statement representing a diagnosis entity 1025e.

Figure 11A:
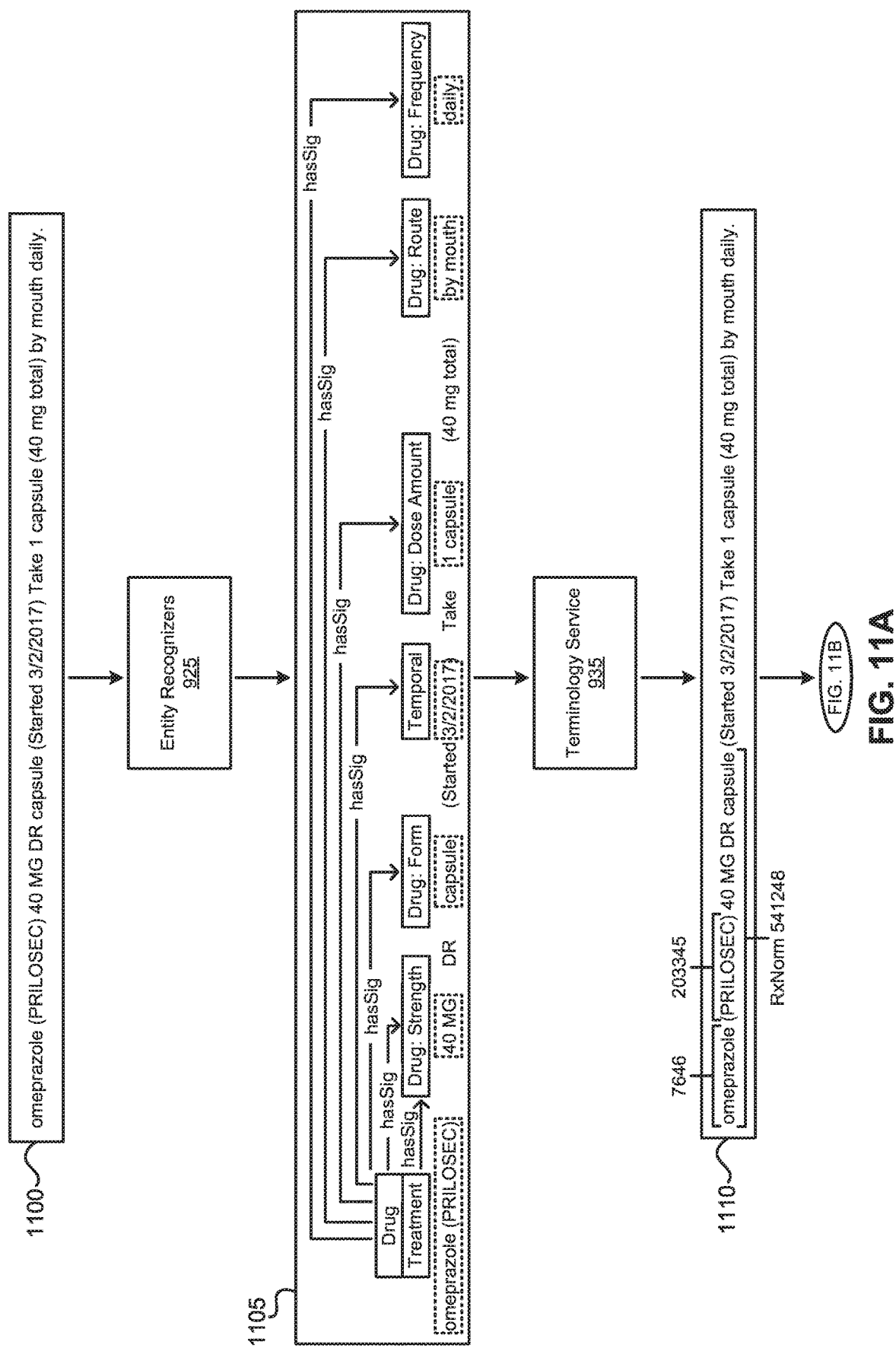
FIG. 11A illustrates an example of extracting a clinical entity from a clinical document according to an embodiment.
Figure 11B:
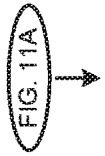
FIG. 11B illustrates an example of an extracted clinical statement according to an embodiment.

FIGS. 11A and 11B illustrate an example of extracting a clinical entity from a clinical document according to some embodiments. As shown in FIG. 11A, entity recognizers 925 receives text 1100, which, in this example, is sent from extraction service 920 (not shown). Text 1100 may be a section of a clinical document or a portion of a section of a clinical document. As mentioned above, extraction service 920 may use one or more NLP pipelines 1015a-e, which can each be implemented by one or more entity recognizers 930a-e, to process a section of a clinical document based on the classification of the section. For this example, extraction service 920 sends text 1100 to clinical NLP pipeline 1015c, which is implemented by implemented by temporal recognizer 930b, clinical recognizer 930c, and cancer recognizer 930d.

FIG. 11A also illustrates text 1105, which is text 1100 after it has been processed by clinical NLP pipeline 1015c. As shown, clinical NLP pipeline 1015c has identified the group of terms "omeprazole (PRILOSEC)" in text 1105 as being a drug and a treatment. Clinical NLP pipeline 1015c has also identified the group of terms "40 MG" as being a strength of a drug and the term "capsule" as being a form of a drug. In addition, clinical NLP pipeline 1015c has identified the term "3/2/2017" as being temporal data. Clinical NLP pipeline 1015c has also identified the group of terms "1 capsule" as being a dose amount of a drug, the group of terms "by mouth" as being a route of administering a drug, and the term "daily" as being a frequency of dosage of a drug. Once extraction service 920 receives text 1105 from clinical NLP pipeline 1015c, extraction service 920 sends it to terminology service 935. Next, terminology service 935 validates, with the use of the data stores configured to store medical codes mentioned above, the identifications of terms and groups of terms in text 1105 by clinical NLP pipeline 1015c as being data associated with certain types of data. Additionally, terminology service 935 determines medical codes for one or more of the validated terms and/or groups of terms and associates them with respective terms and/or groups of terms. In some cases, terminology service 935 can determine and associated a medical code with one validated term. In other cases, terminology service 935 can determine and associated a medical code with several validated terms. FIG. 11A further illustrates text 1110, which is text 1105 after terminology service 935 determines codes for validated terms and/or groups of terms. As shown, for this example, terminology service 935 determined a medical code "7646" for the term "omeprazole," a medical code "203345" for the term "PRILOSEC," and a medical code "RxNorm 541248" for the group of terms "omeprazole (PRILOSEC) 40 MG DR capsule." Terminology service 935 sends text 1110 to extraction service 920 for further processing. Upon receiving text 1110, extraction service 920 generates a clinical statement based on the text 1110.

In some embodiments, clinical statements may include a common set of attributes. For example, a clinical statement that represents a clinical entity may include a statement type attribute that indicates the type of clinical statement (e.g., a patient statement, a provider statement, a medication statement, a procedure statement, a diagnosis statement, a genetic mutation statement, etc.) and a document identifier for identifying the clinical document from which the clinical statement is extracted. Additional and/or different attributes may be used in different embodiments.

In addition to a common set of attributes, clinical statements that represent different types of clinical entities may have different sets of additional attributes in some embodiments. For instance, a clinical statement for a patient entity can include a name attribute for storing the name of a patient and medical record number (MRN) attribute for storing a unique identifier used by a provider that is associated with the patient. For a clinical statement of a provider entity, a name attribute may be used to store the name of a provider and a national provider identifier (NPI) attribute may be used to store a unique identifier associated with the provider. A clinical statement for a medication entity can include the following attributes: a frequency of dosage of a drug, a route of administration of the drug, an amount per dosage of the drug, and a generic name of the drug. Clinical statements for procedure entities may each include a name attribute for storing the name of a procedure and a performed date attribute for storing the date on which the procedure was performed. A clinical statement for a diagnosis entity can include a name attribute for storing the name of the diagnosis. For a clinical statement of a genetic mutation entity, a name attribute may be used to store the name of the genetic mutation. One of ordinary skill in the art will appreciate that the attributes for clinical statements representing different types of clinical entities described above are merely examples. Each type of clinical entity may have additional and/or different attributes in different embodiments.

FIG. 11B illustrates clinical statement 1115, which is the clinical statement generated by extraction service 920 in this example. As shown, clinical statement 1115 includes data structures 1120 and 1125. Data structure 1120 represents the drug identified in text 1110 and includes attributes such as a unique ID, a resource type, a medical code the drug, ingredients of the drug etc. Data structure 1125 represent a clinical statement for a medication clinical entity. As shown, data structure 1125 includes attributes such a unique ID, a date on which the drug was started, a resource type, a reference to the drug (i.e., data structure 1120), a reference to a patient, etc.

Figure 12A:
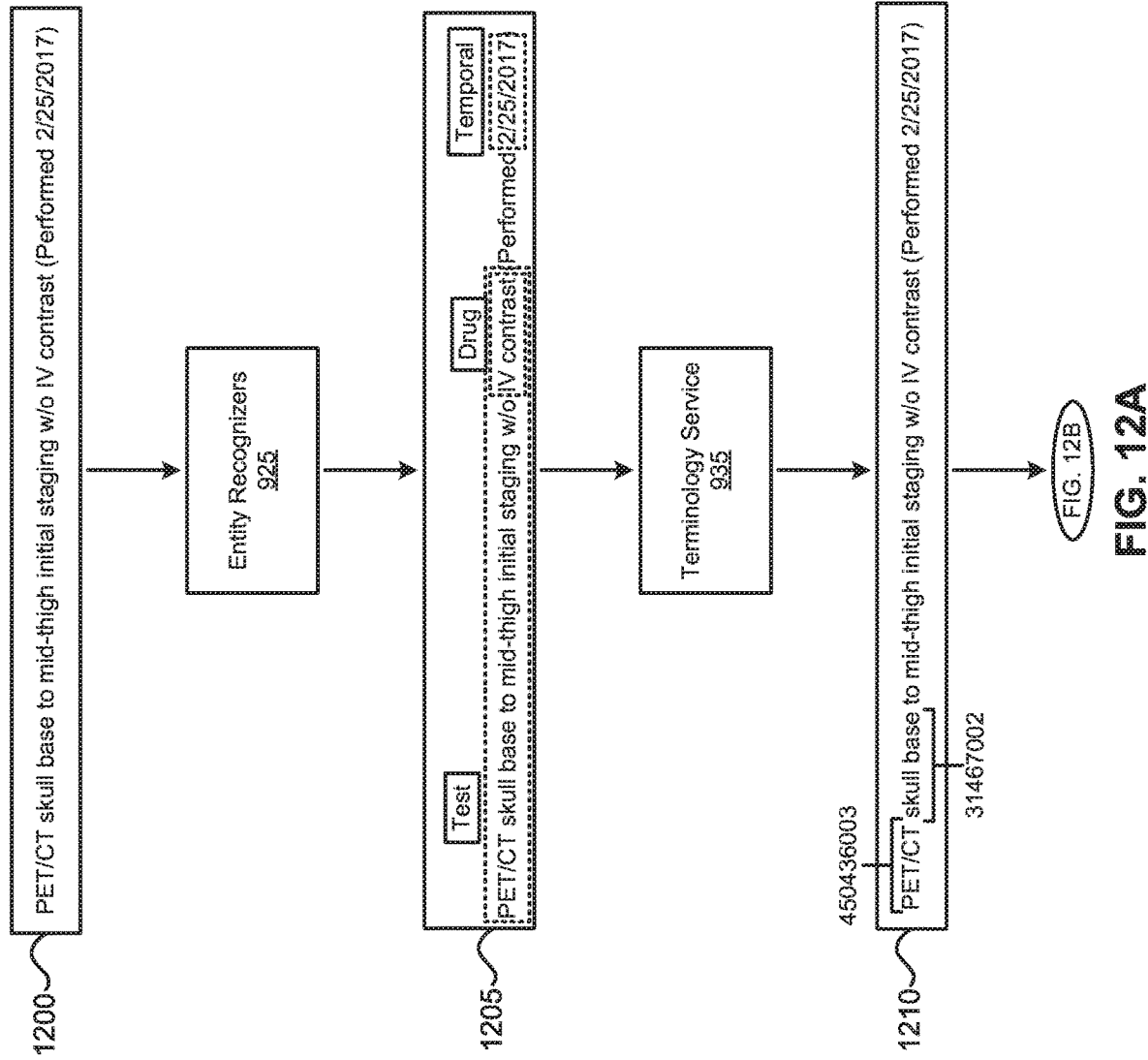
FIG. 12A illustrates another example of extracting a clinical entity from a clinical document according to an embodiment.
Figure 12B:
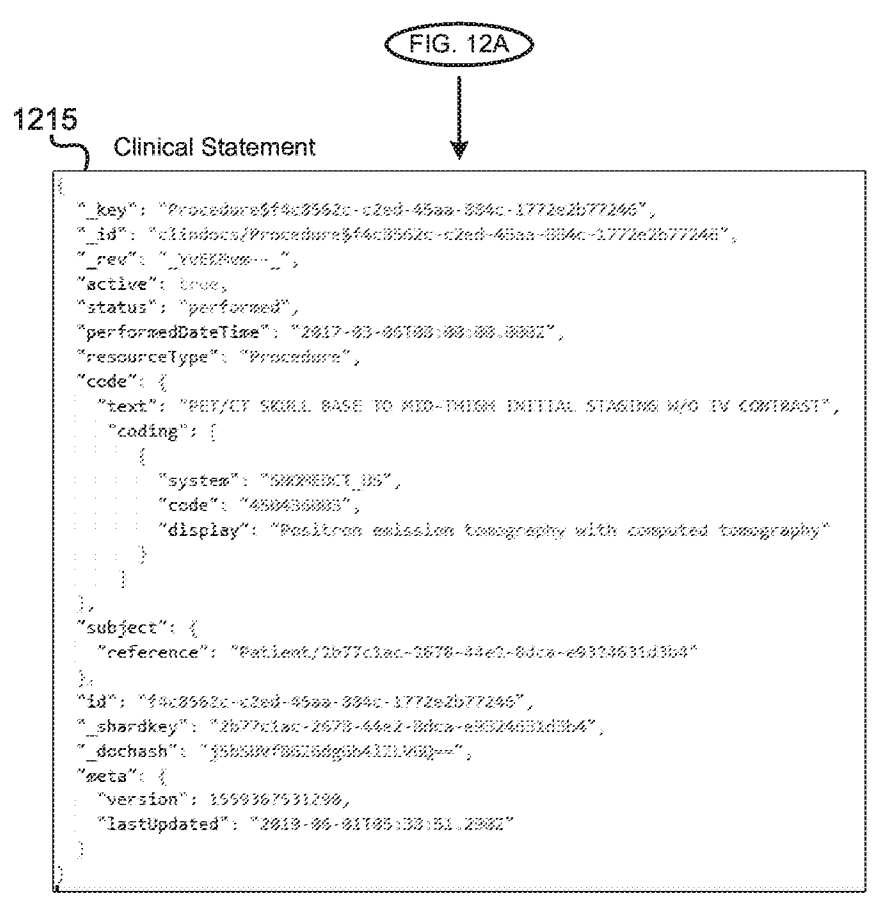

FIGS. 12A and 12B illustrate another example of extracting a clinical entity from a clinical document according to some embodiments. As illustrated in FIG. 12A, entity recognizers 925 receives text 1200, which, in this example, is sent from extraction service 920 (not shown). Text 1200 can be a section of a clinical document or a portion of a section of a clinical document. As mentioned above, extraction service 920 may use one or more NLP pipelines 1015a-e, which can each be implemented by one or more entity recognizers 930a-e, to process a section of a clinical document based on the classification of the section. In this example, extraction service 920 sends text 1200 to clinical NLP pipeline 1015c, which is implemented by implemented by temporal recognizer 930b, clinical recognizer 930c, and cancer recognizer 930d.

FIG. 12A also illustrates text 1205, which is text 1200 after it has been processed by clinical NLP pipeline 1015c. As illustrated, clinical NLP pipeline 1015c has identified the group of terms "PET/CT skull base to mid-thigh initial staging w/o IV contrast" in text 1205 as being a test. Clinical NLP pipeline 1015c has also identified the group of terms "IV contrast" as being a drug. Further, clinical NLP pipeline 1015c has identified the term "2/25/2017" as being temporal data. After receiving text 1205 from clinical NLP pipeline 1015c, extraction service 920 sends it to terminology service 935. Terminology service 935 then validates, with the use of the data stores configured to store medical codes mentioned above, the identifications of terms and groups of terms in text 1205 by clinical NLP pipeline 1015c as being data associated with certain types of data. Terminology service 935 also determines medical codes for one or more of the validated terms and/or groups of terms and associates them with respective terms and/or groups of terms. FIG. 12A also illustrates text 1210, which is text 1205 after terminology service 935 determines codes for validated terms and/or groups of terms. As illustrated, terminology service 935 determined a medical code "450436003" for the term "PET/CT" and a medical code "31467002" for the group of terms "skull base." Next, terminology service 935 sends text 1210 to extraction service 920 for further processing. Once extraction service 920 receives text 1210, extraction service 920 generates a clinical statement based on the text 1210.

FIG. 12B illustrates clinical statement 1215, which is the clinical statement generated by extraction service 920 in this example. As illustrated, clinical statement 1215 is a data structure, which in this example represents the procedure identified in text 1210. Clinical statement 1215 includes attributes such as a unique ID, a resource type, a medical code for the procedure, a reference to a patient, etc.

FIGS. 11A-12B show examples where a clinical statement is generated from a section of a clinical document. In some embodiments, multiple clinical statements may be generated from a section of clinical document. For example, a clinical statement representing a medication and a procedure may be generated for a section classified as a history of present illness section. One of ordinary skill in the art will realize that any number of different clinical statements can be generated from a section of a clinical document.

Figure 13:
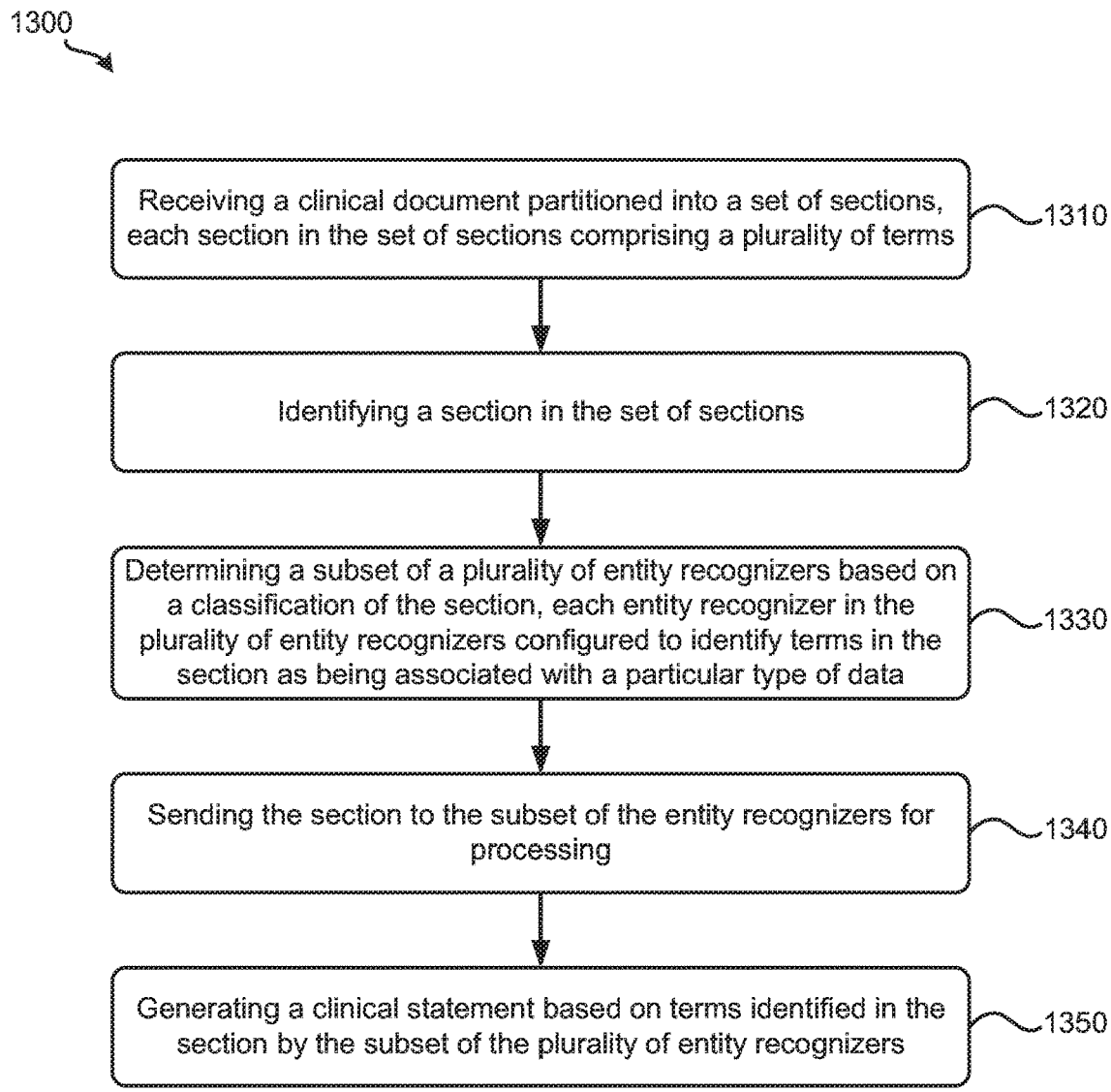
FIG. 13 illustrates a process for extracting clinical entities from a clinical document according to various embodiments.

FIG. 13 illustrates a process 1300 for extracting clinical entities from a clinical document. In some embodiments, extraction process 920 performs process 1300. Process 1300 starts by receiving, at 1310, a clinical document partitioned into a set of sections. Each section in the set of sections includes a plurality of terms. Referring to FIGS. 9 and 10 as an example, extraction service 920 can receive clinical document 1000.

Next, process 1300 identifies, at 1320 a section in the set of sections. Referring to FIGS. 9 and 10 as an example, extraction service 920 can identify one of the sections in clinical document 1000. Then, process 1300 determines, at 1330, a subset of a plurality of entity recognizers based on a classification of the section. Each entity recognizer in the plurality of entity recognizers is configured to identify terms in the section as being associated with a particular type of data. Referring to FIGS. 9 and 10 as an example, extraction service 920 can determine an NLP pipeline 1015, which can be implemented using one or more entity recognizers 930a-e, based on the classification of the section in clinical document 1000.

At 1340, process 1300 sends the section to the subset of the entity recognizers for processing. Referring to FIGS. 9 and 10 as an example, extraction service 920 may send the section to the determined NLP pipeline 1015 for processing. Finally, process 1300 generates, at 1350, a clinical statement based on terms identified in the section by the subset of the plurality of entity recognizers. Referring to FIGS. 9 and 10 as an example, extraction service 920 can generate a clinical statement that represents one of the clinical entities shown in clinical statements 1025 based on terms identified in the section by the determined NLP pipeline 1015.

C. Further Sectionalization Techniques

Figure 17:
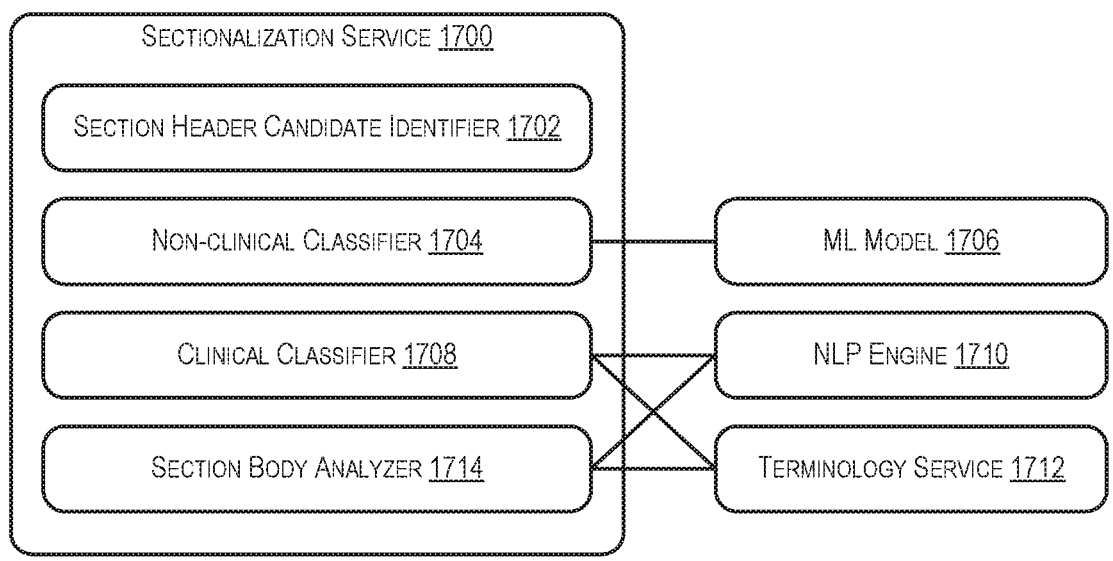
FIG. 17 illustrates another sectionalization service according to an embodiment.

FIG. 17 is a simplified block diagram of another sectionalization service 1700 that may be implemented by platform 102 of FIG. 1 (either in addition to, or in lieu of, sectionalization service 550 of FIG. 5) for sectionalizing clinical documents in accordance with certain embodiments. As shown, sectionalization service 1700 includes a section header candidate identifier 1702, a non-clinical classifier 1704 that is communicatively coupled with a ML model 1706, a clinical classifier 1708 that is communicatively coupled with an NLP engine 1710 and a terminology service 1712, and a section body analyzer 1714 that is also communicatively coupled with NLP engine 1710 and terminology service 1712. In some embodiments, terminology service 1712 may be the same terminology service used by the extraction block of platform 102 for performing entity extraction.

At a high level, sectionalization service 1700 can sectionalize a clinical document on a page-by-page basis, where each page is processed according to three phases: (1) a section header candidate identification phase, (2) a section header candidate classification phase, and (3) a section body analysis and roll-up phase. In phase (1), sectionalization service 1700 can use section header candidate identifier 1702 to identify possible/likely section or sub-section headers (i.e., section header candidates) within the page, as well as a section hierarchy level for each candidate. In one set of embodiments, section header candidate identifier 1702 can perform this task using a set of fixed rules that are based on one or more visual formatting properties of the clinical document. This fixed rule-based approach is largely similar to the process of identifying "significant signatures" described with respect to sectionalization service 550 of FIG. 5.

In other embodiments, section header candidate identifier 1702 can perform this task using an entropy-based approach that involves, among other things, (1) calculating an "entropy score" for each line of text in the page, the entropy score being computed as a weighted average of values for one or more stylistic/structural attributes of the line, (2) comparing the per-line entropy scores with a threshold to determine whether each line of text should be identified as a section header candidate or not, and (3) mapping each line's entropy score to a cluster of entropy scores in the clinical document to determine an appropriate section hierarchy level for that line. This entropy-based approach is described in further detail in commonly-owned U.S. Patent Application "ENTROPY-BASED IDENTIFICATION OF SECTION HEADER CANDIDATES IN ELECTRONIC DOCUMENTS," whose serial/patent number information is provided in the "Cross-References to Related Applications" section above.

In phase (2), sectionalization service 1700 can use non-clinical classifier 1704 and/or clinical classifier 1708 to try and classify each section header candidate identified in phase (1) as corresponding to one of a set of predefined section types understood by platform 102. These predefined section types can generally pertain to concepts/activities/events/parties/etc. that are relevant to the provisioning of healthcare to a patient. The following is an exemplary list of such predefined section types according to an embodiment:

Medications
Diagnosis
Procedure
Lab results
Gene report
Allergies
Vitals
Immunization
Demographics
Organization
Provider
Reason for visit
History of present illness In various embodiments, classifiers 1704 and 1708 can be designed to approach the classification task in phase (2) from two different perspectives: a non-clinical perspective and a clinical perspective. In particular, non-clinical classifier 1704 can be configured to accurately classify non-clinical section header candidates (i.e., section header candidates that contain solely non-clinical terms, such as "Current medications," "Lab results of 9/1/17," etc.) through the use of ML model 1706, which is trained to (1) receive an input text string comprising non-clinical terms and (2) output a set of confidence scores for each of the predefined section types noted above, each confidence score indicating the likelihood that the input text string can be mapped to the corresponding section type. For example, upon receiving the section header candidate "Current medications," non-clinical classifier 1704 can pass this candidate as input to ML model 1706, which may output the set of per-section type confidence scores noted in Table 1 below. As shown here, the section type "Medications" is associated with the highest confidence score, which indicates that ML model 1706 has determined "Medications" is the most likely classification/section type for "Current medications."

TABLE 1

| Section Type | Confidence Score |
|---|---|
| Medications | 0.9 |
| Diagnosis | 0.3 |
| Procedure | 0.4 |
| Lab results | 0.3 |
| Gene report | 0.2 |
| Allergies | 0.4 |
| Vitals | 0.2 |
| Immunization | 0.5 |
| Demographics | 0.1 |
| Organization | 0.1 |
| Provider | 0.1 |
| Reason for visit | 0.3 |

Non-clinical classifier 1704 can then classify the section header candidate "Current medications" as corresponding to the highest-scoring section type "Medications" if that section type's confidence score is above some threshold (e.g., 0.7 or 70%).

In contrast, clinical classifier 1708 can be configured to accurately classify clinical section header candidates (i.e., section header candidates that contain one or more clinical terms such as a specific medication name, a specific lab result name, etc.) through the use of NLP engine 1710 and terminology service 1712. In one set of embodiments, upon receiving a section header candidate to be classified, clinical classifier 1708 can first pass the candidate to NLP engine 1710, which can use NLP-based named entity recognition to identify instances of clinical entities in the candidate text. For example, in the section header candidate "CBC Panel of 8/23/19," NLP engine 1710 may identify "CBC Panel" as an instance of the clinical entity "lab test." Clinical classifier 1708 can subsequently pass the clinical entity results found by NLP engine 1710 to terminology service 1712, which can perform a lookup into one or more clinical terminology databases to confirm/verify that the results from NLP engine 1710 are correct. For example, terminology service 1712 may access a lab tests database and return a confirmation/verification to clinical classifier 1708 that the term "CBC Panel" is, in fact, a "procedure" with a certain degree of confidence (e.g., 80% or 0.8). Clinical classifier 1708 can then classify the section header candidate "CBC Panel of 8/23/19" as corresponding to the section type "Procedure" if the clinical entity confidence score returned by terminology service 1712 is above some threshold (which may be the same as, or different from, the threshold used by non-clinical classifier 1704).

Through the application of these two different classifiers in phase (2) (i.e., non-clinical classifier 1708 tailored to classifying non-clinical section header candidates and clinical classifier 1708 tailored to classifying clinical section header candidates), sectionalization service 1700 can advantageously increase the accuracy of the classification task over approaches that use a single, general-purpose classifier.

In phase (3), sectionalization service 1700 can use section body analyzer 1714 to analyze the body content (i.e., section bodies) of the section header candidates that have been successfully classified as one of the predefined section types and, upon receiving the results generated by analyzer 1714 for a given section body, "roll-up" that information to the section header level in order to modify/override the section type and/or corresponding confidence score determined for the section header in phase (2), if appropriate. In one set of embodiments, section body analyzer 1714 can execute its analysis by employing the same NLP engine 1710 and terminology service 1712 used by clinical classifier 1708. For example, upon receiving a section body B corresponding to a section header H, section body analyzer 1714 can first pass the body text for B to NLP engine 1710 to recognize clinical entities in the body text, and then pass the recognized entities to terminology service 1712 for confirmation. Section body analyzer 1714 can subsequently generate and provide a clinical entity list to sectionalization service 1700 that identifies (1) the confirmed clinical entities found in the body text for B per NLP engine 1710/terminology service 1712, and (2) an "appearance score" for each confirmed clinical entity indicating, e.g., the percentage of the total number of clinical entity instances found in B that are instances of that entity. For example, if 10 clinical entity instances are found in B and 5 of those are an instance of a "medication," the appearance score for the clinical entity "medication" will be 50% or 0.5.

Upon receiving this clinical entity list for section body B from section body analyzer 1714, sectionalization service 1700 can compare the information therein to the section type and corresponding confidence score previously determined for the body's section header H. Sectionalization service 1700 can then apply one or more predefined roll-up rules to possibly modify the header-level section type and/or confidence score based on the body-level clinical entity list. As one example, if the section type and confidence score previously determined for section header H is "Medications" and 0.6 and the clinical entity list for section body B indicates that 90% of the clinical entities found in section body B are "procedures," then sectionalization service 1700 may, according to one roll-up rule, override the section type from "Medications" to "Procedures." As another example, if the section type and confidence score previously determined for section header H is "Lab tests" and 0.5 and the clinical entity list for section body B indicates that 80% of the clinical entities found in section body B are "lab tests," then sectionalization service 1700 may, according to another roll-up rule, keep the section type of "Lab tests" and increase its confidence score to some weighted or un-weighted average of 0.5 and 0.8 (e.g., 0.65). The exact nature of these rollup rules can vary depending on the implementation and the content of the clinical document corpus processed by platform 102.

In certain embodiments, sectionalization service 1700 can perform phase (3) in a bottom-up manner based on the section hierarchy levels determined via section header candidate identifier 1702 in phase (1)—in other words, sectionalization service 1700 can process all of the section bodies for the lowest level sections/section headers in the page, and then process all of the section bodies for the next lowest level sections/section headers in the page, and so on. In addition, at the time of rolling-up the clinical entity list information for a given section body B to its section header H, sectionalization service 1700 can further take into account the section types/confidence scores of any sub-sections directly under H. This allows sectionalization service 1700 to update the section type and confidence score of section header H based on both its body content and any sub-sections within that section.

Finally, at the conclusion of phase (3), sectionalization service 1700 can record the section information determined above for the current page (e.g., section headers/bodies and corresponding section types and confidence scores) and repeat these phases for additional pages in the clinical document until all of the document's pages have been sectionalized.

The following sub-sections of the present disclosure provide additional details regarding the sectionalization processing that may be performed by sectionalization service 1700 and its constituent components according to certain embodiments. It should be appreciated that the service architecture shown in FIG. 17 is illustrative and not intended to limit embodiments of the present disclosure. For example, although ML model 1706, NLP engine 1710, and terminology service 1712 are shown as being external to sectionalization service 1700 (which can facilitate the re-use of these components by other services/entities of platform 102), in some embodiments one or more of these components may be directly incorporated into sectionalization service 1700. Further, the functionality attributed to a particular component of service 1700 may be split into multiple components, components may be combined, and so on. One of ordinary skill in the art will recognize other variations, modifications, and alternatives.

C.1 Sectionalization Workflow

Figure 18A:
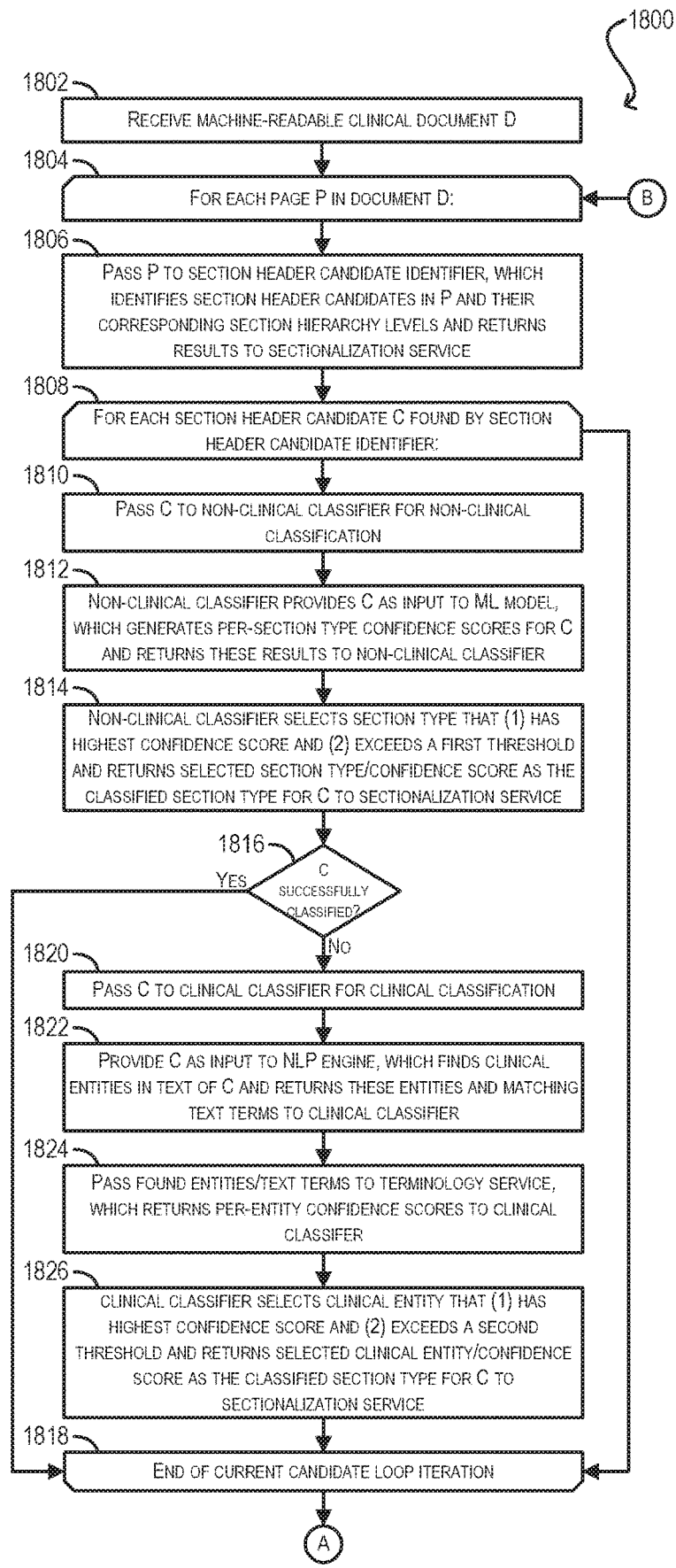
FIGS. 18A and 18B illustrate a workflow that may be executed by the sectionalization service of FIG. 17 for sectionalizing an electronic document according to an embodiment.
Figure 18B:
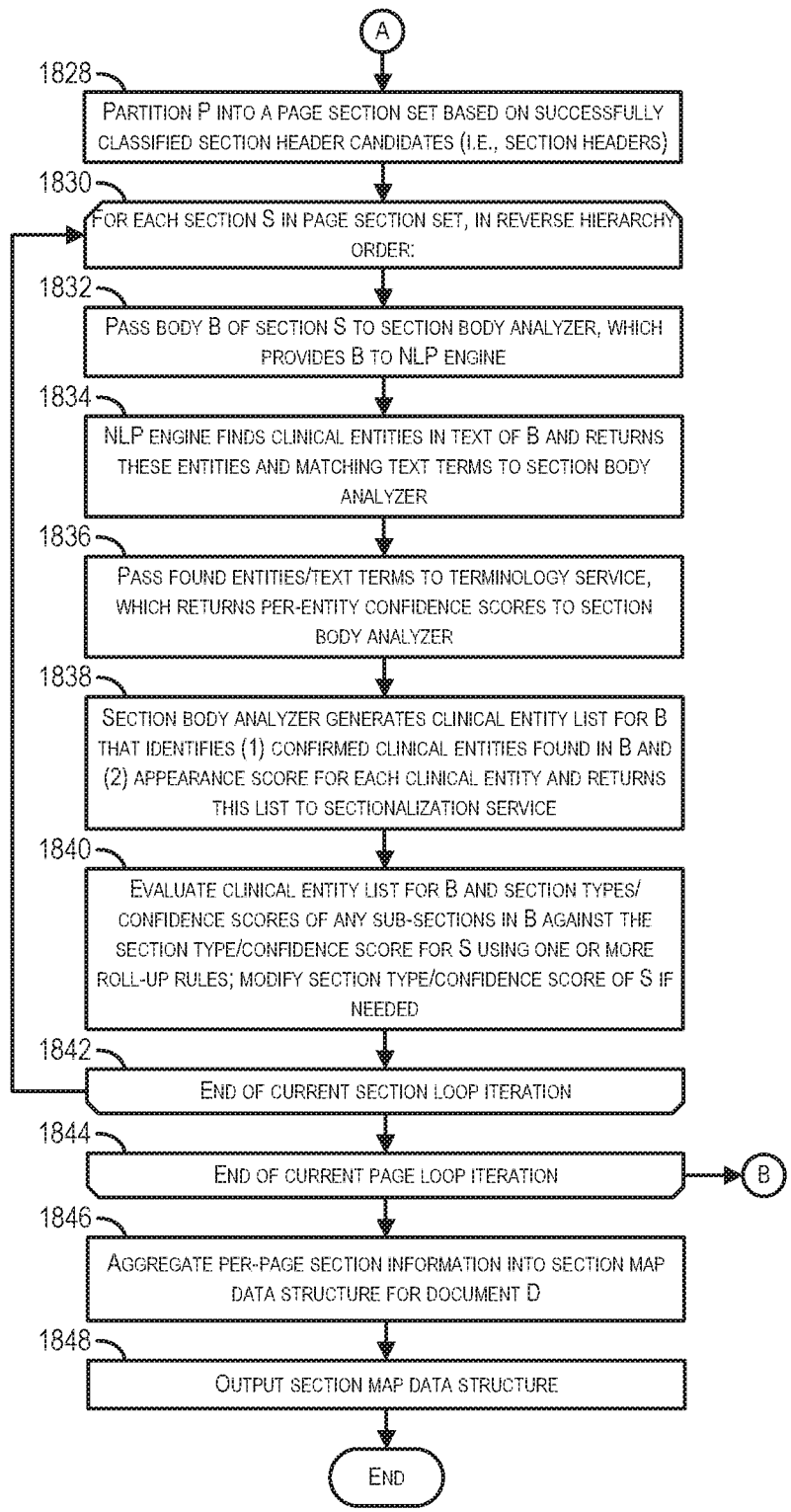

FIGS. 18A and 18B depict a workflow 1800 that can be executed by sectionalization service 1700 and components 1702-1714 for sectionalizing a given clinical document D according to certain embodiments. Workflow 1800 assumes that document D is in a machine-readable format and thus the text content of document D and its associated layout/formatting properties can be read by sectionalization service 1700. Flowchart 1800 also assumes that document D is paginated (i.e., divided into pages), which enables page-by-page processing of the document. If document D is not in paginated form at the time of receipt by sectionalization service 1700, service 1700 may paginate document D prior to the initiation of workflow 1800 using any pagination algorithm known in the art.

Starting with blocks 1802 and 1804 of FIG. 18A, sectionalization service 1700 can receive clinical document D and enter a loop for each page P of the document. Within this first loop, sectionalization service 1700 can pass page P to section header candidate identifier 1702, which can identify section header candidates in page P and their corresponding section hierarchy levels (as described above) and return these results to sectionalization service 1700 (block 1806).

Sectionalization service 1700 can then enter a loop for each section header candidate C found by section header candidate identifier 1702 (block 1808). Within this second loop, sectionalization service 1700 can first pass candidate C to non-clinical classifier 1704 to try and perform non-clinical classification of C (block 1810). Upon receiving candidate C, non-clinical classifier 1704 can provide C as input to ML model 1706, which can generate a confidence score for each of the predefined section types mentioned previously (each confidence score indicating the likelihood that candidate C corresponds to that section type) and can return these per-section type confidence scores to non-clinical classifier 1704 (block 1812).

At block 1814, non-clinical classifier 1704 can select the section type that (1) has the highest confidence score returned by ML model 1706 and (2) exceeds a predefined first threshold and can return the selected section type (and confidence score) to sectionalization service 1700 as being the classified section type for candidate C. If none of the confidence scores output by ML model 1706 are above the predefined first threshold, non-clinical classifier 1704 can return an indication that candidate C cannot be classified.

Sectionalization service 1700 can then check whether non-clinical classifier 1704 has successfully classified candidate C (i.e., returned a section type and confidence score) (block 1816). If the answer is yes, sectionalization service 1700 can proceed to the end of the current candidate loop iteration (block 1818) and return to the top of the loop (block 1808) to process any additional section header candidates.

On the other hand, if the answer at block 1816 is no, sectionalization service 1700 can pass candidate C to clinical classifier 1708 to try and perform clinical classification of C (block 1820). Upon receiving candidate C, clinical classifier 1708 can provide C as input to NLP engine 1710, which can use named entity recognition to find any clinical entities in the text of candidate C and can return the found clinical entities (and text terms corresponding to those found entities) to clinical classifier 1708 (block 1822).

Clinical classifier 1708 can subsequently pass these clinical entities/text terms to terminology service 1712 for confirmation, and terminology service 1712 can return a result list to clinical classifier 1708 indicating, for each text term T identified to be a clinical entity E by NLP engine 1710, a confidence score indicating the likelihood that term T is in fact an instance of entity E (block 1824).

At block 1826, clinical classifier 1708 can select, from the result list received from terminology service 1712, the clinical entity that (1) has the highest confidence score and (2) exceeds a predefined second threshold and can return the selected clinical entity (and confidence score) to sectionalization service 1700 as being the classified section type for candidate C. If none of the confidence scores generated by terminology service 1712 are above the predefined second threshold, clinical classifier 1708 can return an indication that candidate C cannot be classified.

Sectionalization service 1700 can then reach end of the current candidate loop iteration (block 1818) and return to the top of the loop (block 1808) to process any additional section header candidates. Once all section header candidates have been processed, workflow 1800 can proceed to FIG. 18B.

At block 1828 of FIG. 18B, sectionalization service 1700 can partition page P into one or more sections (i.e., a page section set) based on the section header candidates that have been successfully classified via either non-clinical classifier 1704 or clinical classifier 1708. Each successfully classified section header candidate is referred to as a section header. For example, if three section header candidates C1, C2, and C3 have been successfully classified (and thus are now section headers H1, H2, and H3), sectionalization service 1700 can partition page P into a first section S1 spanning from H1 to H2, a second section S2 spanning from H2 to H3, and a third section S3 spanning from H3 to the end of the page. In various embodiments, this partitioning step can include marking each section in the page section set as having the section type and confidence score determined for its corresponding section header and identifying the body of each section (i.e., all of the content in the section between the section header and the next section header in the page).

Sectionalization service 1700 can thereafter enter a loop for each section S in the page section set to validate the section's section type/confidence score via an analysis of its body B (block 1830). In this loop, sectionalization service 1700 can process the sections in a reverse section hierarchy order (i.e., from lowest-level section to highest-level section) per the section hierarchy levels received from section header candidate identifier 1702 at block 1806.

Within the loop, sectionalization service 1700 can first pass section body B of section S to section body analyzer 1714, which in turn can provide body B to NLP engine 1710 (block 1832). Upon receiving body B, NLP engine 1710 can use named entity recognition to find any clinical entities in the text of body B and can return the found clinical entities (and text terms corresponding to those found entities) to section body analyzer 1714 (block 1834).

Section body analyzer 1714 can subsequently pass these clinical entities/text terms to terminology service 1712 for confirmation, and terminology service 1712 can return a result list to section body analyzer 1714 indicating, for each text term T identified to be a clinical entity E by NLP engine 1710, a confidence score indicating the likelihood that term T is in fact an instance of entity E (block 1836).

From the results returned by NLP engine 1710 and NLP engine 1712, section body analyzer 1714 can generate a clinical entity list that, as mentioned previously, identifies (1) the confirmed clinical entities found in the text of body B per NLP engine 1710/terminology service 1712, and (2) an appearance score for each confirmed clinical entity indicating the percentage of the total number of clinical entity instances found in B that are instances of that entity, and can return this clinical entity list to sectionalization service 1700 (block 1838).

Sectionalization service 1700 can then evaluate, using one or more roll-up rules, the clinical entity list and the section types/confidence scores of any sub-sections within section S against the section type/confidence score for S. Based on this evaluation, sectionalization service 1700 can modify the section type and/or confidence score for S, if dictated by the roll-up rules (block 1840).

At block 1842, sectionalization service 1700 can reach the end of the current section loop iteration and return to the top of that loop (block 1830) process additional sections in the page section set for page P. Further, once all of the sections in the page section set have been processed, sectionalization service 1700 can reach the end of the current page loop iteration (block 1844) and can return to the top of that loop (block 1804) to process additional pages in document D.

Once all of the pages in document D have been processed, sectionalization service 1700 can aggregate the per-page section information determined above into a section map data structure for document D (block 1846). In various embodiments, this section map data structure can include an entry for every section found in document D, and each entry can identify the section's section type, confidence score, section span (i.e., range of lines in the document covered by the section), and potentially other section-related information (e.g., the clinical entity list for the section body as generated by section body analyzer 1714, etc.). Finally, at block 1848, sectionalization service 1700 can output the section map data structure for use by a downstream consumer (e.g., the extraction block of platform 102) and workflow 1800 can end.

It should be appreciated that workflow 1800 is illustrative and various modifications are possible. For example, although workflow 1800 indicates that sectionalization 1700 first attempts to classify a section header candidate using non-clinical classifier 1704 and then, if that is not successful, attempts to classify the section header candidate using clinical classifier 1708, in some embodiments this order can be reversed (e.g., clinical classifier 1708 be applied first). In other embodiments, sectionalization service 1700 can apply both classifiers to every section header candidate and select the output of one classifier as the correct section type for the candidate based on some criteria.

Further, although workflow 1800 indicates that the processing of pages in document D are performed in a sequential manner via page loop 1804, in some embodiments sectionalization service 1700 may process the pages in a parallel manner via, e.g., multiple processing threads or cores of one or more computer systems. One of ordinary skill in the art will recognize other variations, modifications, and alternatives.

C.2 Merging Section Content Across Pages

One complication with page-based sectionalization workflow 1800 of FIGS. 18A and 18B is that, for a section S which spans across multiple pages P1, P2, . . . PN, any content for section S which appears on pages P2 onward will not be preceded by the header for S on those specific pages within the document (because the header for S will appear only at the start of S on page P1). As a result, the content for section S on pages P2-PN will not be identified as being part of S in the section map data structure generated by sectionalization service 1700.

Figure 19:
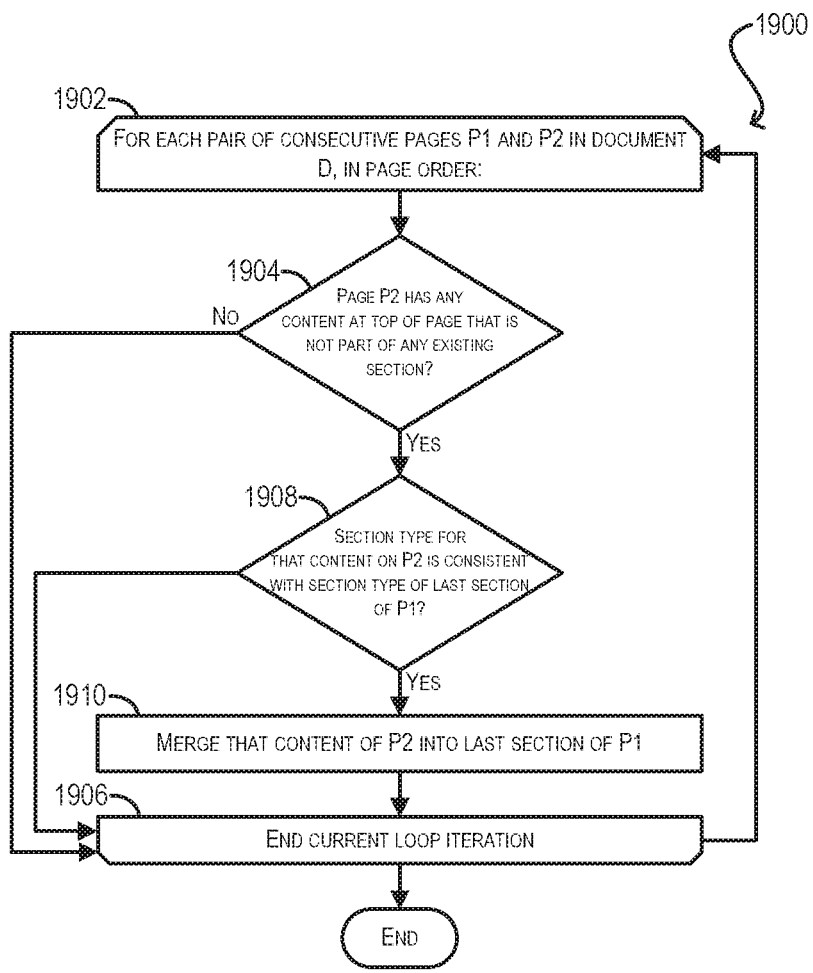
FIG. 19 illustrates a workflow that may be executed by the sectionalization service of FIG. 17 for merging section content across pages according to an embodiment.

To address this issue, FIG. 19 depicts a workflow 1900 can be executed by sectionalization service 1700 within workflow 1800, after block 1846 (i.e., aggregation of per-page section information into the section map data structure) but prior to block 1848 (i.e., outputting of the section map data structure), for merging such "orphaned" content back into its correct section.

At block 1902 of workflow 1900, sectionalization service 1700 can enter a loop for each pair of consecutive pages P1 and P2 in document, starting from page 1 of the document (i.e., in page order).

Within this loop, sectionalization service 1700 can check whether page P2 has any content of the top of the page that is not a part of any existing section in the document's section map data structure (block 1904). If the answer is no, sectionalization service 1700 can proceed to the end of the current loop iteration (block 1906).

If the answer at block 1904 is yes, sectionalization service 1700 can further check whether the section type for that content on page P2 is consistent with (e.g., the same as) the section type of the last section found on page P1 (block 1908). This step can involve, e.g., applying section body analyzer 1714 to the content in order to determine its appropriate section type. If the answer is no, sectionalization service 1700 can proceed to the end of the current loop iteration as above.

However, if the answer at block 1908 is yes, sectionalization service 1700 can add that content in page P2 to the last section of page P1 in the section map data structure, thereby merging that content into P1's last section (block 1910).

Finally, sectionalization service 1700 can reach the end of the current loop iteration and return to the top of the loop (block 1902) to process additional pairs of consecutive pages in document D. Once all pairs of consecutive pages have been processed, workflow 1900 can end.

Example Computer Hardware

Figure 14:
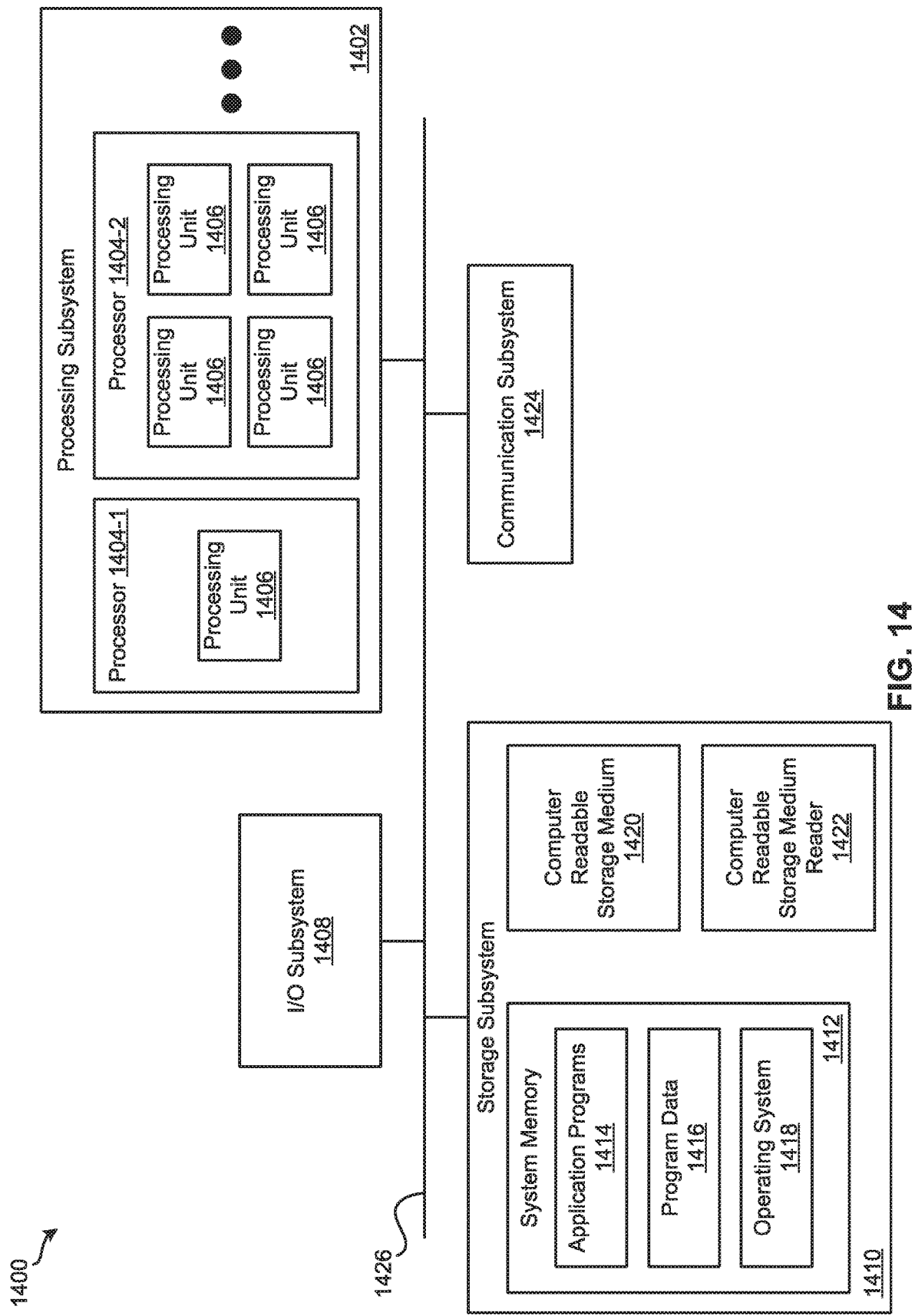
FIG. 14 illustrates an exemplary computer system, in which various embodiments may be implemented.

FIG. 14 illustrates an example computer system 1400 for implementing various embodiments described above. For example, computer system 1400 may be used to implement client devices for accessing a platform according to various embodiments. Computer system 1400 may be a desktop computer, a laptop, a server computer, or any other type of computer system or combination thereof. In addition, computer system 1400 can implement many of the operations, methods, and/or processes described above. As shown in FIG. 14, computer system 1400 includes processing subsystem 1402, which communicates, via bus subsystem 1426, with input/output (I/O) subsystem 1408, storage subsystem 1410 and communication subsystem 1424.

Bus subsystem 1426 is configured to facilitate communication among the various components and subsystems of computer system 1400. While bus subsystem 1426 is illustrated in FIG. 14 as a single bus, one of ordinary skill in the art will understand that bus subsystem 1426 may be implemented as multiple buses. Bus subsystem 1426 may be any of several types of bus structures (e.g., a memory bus or memory controller, a peripheral bus, a local bus, etc.) using any of a variety of bus architectures. Examples of bus architectures may include an Industry Standard Architecture (ISA) bus, a Micro Channel Architecture (MCA) bus, an Enhanced ISA (EISA) bus, a Video Electronics Standards Association (VESA) local bus, a Peripheral Component Interconnect (PCI) bus, a Universal Serial Bus (USB), etc.

Processing subsystem 1402, which can be implemented as one or more integrated circuits (e.g., a conventional microprocessor or microcontroller), controls the operation of computer system 1400. Processing subsystem 1402 may include one or more processors 1404. Each processor 1404 may include one processing unit 1406 (e.g., a single core processor such as processor 1404-1) or several processing units 1406 (e.g., a multicore processor such as processor 1404-2). In some embodiments, processors 1404 of processing subsystem 1402 may be implemented as independent processors while, in other embodiments, processors 1404 of processing subsystem 1402 may be implemented as multiple processors integrate into a single chip or multiple chips. Still, in some embodiments, processors 1404 of processing subsystem 1402 may be implemented as a combination of independent processors and multiple processors integrated into a single chip or multiple chips.

In some embodiments, processing subsystem 1402 can execute a variety of programs or processes in response to program code and can maintain multiple concurrently executing programs or processes. At any given time, some or all of the program code to be executed can reside in processing subsystem 1402 and/or in storage subsystem 1410. Through suitable programming, processing subsystem 1402 can provide various functionalities, such as the functionalities described above.

I/O subsystem 1408 may include any number of user interface input devices and/or user interface output devices. User interface input devices may include a keyboard, pointing devices (e.g., a mouse, a trackball, etc.), a touchpad, a touch screen incorporated into a display, a scroll wheel, a click wheel, a dial, a button, a switch, a keypad, audio input devices with voice recognition systems, microphones, image/video capture devices (e.g., webcams, image scanners, barcode readers, etc.), motion sensing devices, gesture recognition devices, eye gesture (e.g., blinking) recognition devices, biometric input devices, and/or any other types of input devices.

User interface output devices may include visual output devices (e.g., a display subsystem, indicator lights, etc.), audio output devices (e.g., speakers, headphones, etc.), etc. Examples of a display subsystem may include a cathode ray tube (CRT), a flat-panel device (e.g., a liquid crystal display (LCD), a plasma display, etc.), a projection device, a touch screen, and/or any other types of devices and mechanisms for outputting information from computer system 1400 to a user or another device (e.g., a printer).

As illustrated in FIG. 14, storage subsystem 1410 includes system memory 1412, computer-readable storage medium 1420, and computer-readable storage medium reader 1422. System memory 1412 may be configured to store software in the form of program instructions that are loadable and executable by processing subsystem 1402 as well as data generated during the execution of program instructions. In some embodiments, system memory 1412 may include volatile memory (e.g., random access memory (RAM)) and/or non-volatile memory (e.g., read-only memory (ROM), programmable read-only memory (PROM), erasable programmable read-only memory (EPROM), electrically erasable programmable read-only memory (EEPROM), flash memory, etc.). System memory 1412 may include different types of memory, such as static random access memory (SRAM) and/or dynamic random access memory (DRAM). System memory 1412 may include a basic input/output system (BIOS), in some embodiments, that is configured to store basic routines to facilitate transferring information between elements within computer system 1400 (e.g., during start-up). Such a BIOS may be stored in ROM (e.g., a ROM chip), flash memory, or any other type of memory that may be configured to store the BIOS.

As shown in FIG. 14, system memory 1412 includes application programs 1414, program data 1416, and operating system (OS) 1418. OS 1418 may be one of various versions of Microsoft Windows, Apple Mac OS, Apple OS X, Apple macOS, and/or Linux operating systems, a variety of commercially-available UNIX or UNIX-like operating systems (including without limitation the variety of GNU/Linux operating systems, the Google Chrome® OS, and the like) and/or mobile operating systems such as Apple iOS, Windows Phone, Windows Mobile, Android, BlackBerry OS, Blackberry 10, and Palm OS, WebOS operating systems.

Computer-readable storage medium 1420 may be a non-transitory computer-readable medium configured to store software (e.g., programs, code modules, data constructs, instructions, etc.). Many of the components and/or processes described above may be implemented as software that when executed by a processor or processing unit (e.g., a processor or processing unit of processing subsystem 1402) performs the operations of such components and/or processes. Storage subsystem 1410 may also store data used for, or generated during, the execution of the software.

Storage subsystem 1410 may also include computer-readable storage medium reader 1422 that is configured to communicate with computer-readable storage medium 1420. Together and, optionally, in combination with system memory 1412, computer-readable storage medium 1420 may comprehensively represent remote, local, fixed, and/or removable storage devices plus storage media for temporarily and/or more permanently containing, storing, transmitting, and retrieving computer-readable information.

Computer-readable storage medium 1420 may be any appropriate media known or used in the art, including storage media such as volatile, non-volatile, removable, non-removable media implemented in any method or technology for storage and/or transmission of information. Examples of such storage media includes RAM, ROM, EEPROM, flash memory or other memory technology, compact disc read-only memory (CD-ROM), digital versatile disk (DVD), Blu-ray Disc (BD), magnetic cassettes, magnetic tape, magnetic disk storage (e.g., hard disk drives), Zip drives, solid-state drives (SSD), flash memory card (e.g., secure digital (SD) cards, CompactFlash cards, etc.), USB flash drives, or any other type of computer-readable storage media or device.

Communication subsystem 1424 serves as an interface for receiving data from, and transmitting data to, other devices, computer systems, and networks. For example, communication subsystem 1424 may allow computer system 1400 to connect to one or more devices via a network (e.g., a personal area network (PAN), a local area network (LAN), a storage area network (SAN), a campus area network (CAN), a metropolitan area network (MAN), a wide area network (WAN), a global area network (GAN), an intranet, the Internet, a network of any number of different types of networks, etc.). Communication subsystem 1424 can include any number of different communication components. Examples of such components may include radio frequency (RF) transceiver components for accessing wireless voice and/or data networks (e.g., using cellular technologies such as 2G, 3G, 4G, 5G, etc., wireless data technologies such as Wi-Fi, Bluetooth, ZigBee, etc., or any combination thereof), global positioning system (GPS) receiver components, and/or other components. In some embodiments, communication subsystem 1424 may provide components configured for wired communication (e.g., Ethernet) in addition to or instead of components configured for wireless communication.

One of ordinary skill in the art will realize that the architecture shown in FIG. 14 is only an example architecture of computer system 1400, and that computer system 1400 may have additional or fewer components than shown, or a different configuration of components. The various components shown in FIG. 14 may be implemented in hardware, software, firmware or any combination thereof, including one or more signal processing and/or application specific integrated circuits.

Figure 15:
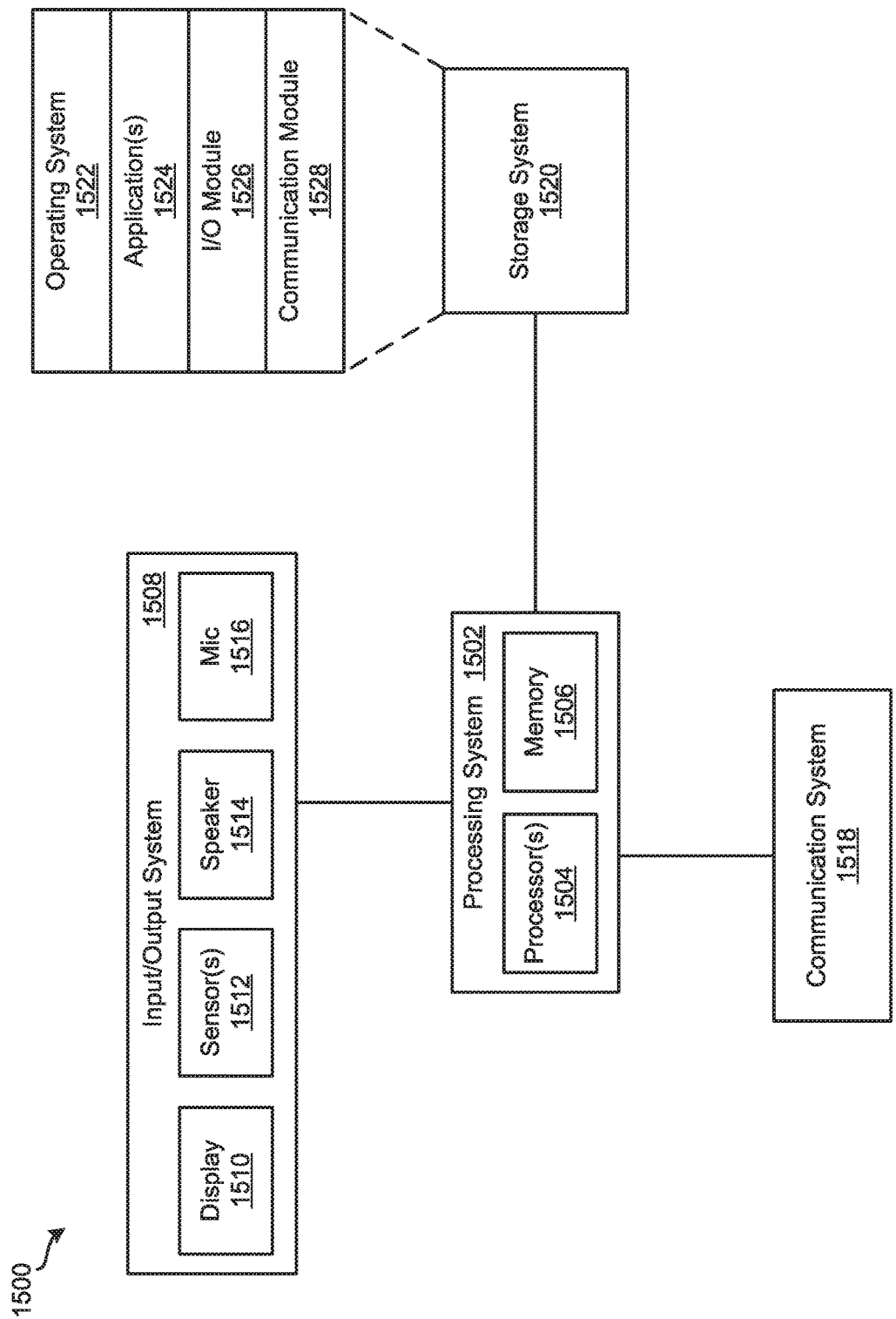
FIG. 15 illustrates an exemplary computing device, in which various embodiments may be implemented.

FIG. 15 illustrates an exemplary computing device 1500 for implementing various embodiments described above. Computing device 1500 may be a cellphone, a smartphone, a wearable device, an activity tracker or manager, a tablet, a personal digital assistant (PDA), a media player, or any other type of mobile computing device or combination thereof. As shown in FIG. 15, computing device 1500 includes processing system 1502, input/output (I/O) system 1508, communication system 1518, and storage system 1520. These components may be coupled by one or more communication buses or signal lines.

Processing system 1502, which can be implemented as one or more integrated circuits (e.g., a conventional microprocessor or microcontroller), controls the operation of computing device 1500. As shown, processing system 1502 includes one or more processors 1504 and memory 1506. Processors 1504 are configured to run or execute various software and/or sets of instructions stored in memory 1506 to perform various functions for computing device 1500 and to process data.

Each processor of processors 1504 may include one processing unit (e.g., a single core processor) or several processing units (e.g., a multicore processor). In some embodiments, processors 1504 of processing system 1502 may be implemented as independent processors while, in other embodiments, processors 1504 of processing system 1502 may be implemented as multiple processors integrate into a single chip. Still, in some embodiments, processors 1504 of processing system 1502 may be implemented as a combination of independent processors and multiple processors integrated into a single chip.

Memory 1506 may be configured to receive and store software (e.g., operating system 1522, applications 1524, I/O module 1526, communication module 1528, etc. from storage system 1520) in the form of program instructions that are loadable and executable by processors 1504 as well as data generated during the execution of program instructions. In some embodiments, memory 1506 may include volatile memory (e.g., random access memory (RAM)), non-volatile memory (e.g., read-only memory (ROM), programmable read-only memory (PROM), erasable programmable read-only memory (EPROM), electrically erasable programmable read-only memory (EEPROM), flash memory, etc.), or a combination thereof.

I/O system 1508 is responsible for receiving input through various components and providing output through various components. As shown for this example, I/O system 1508 includes display 1510, one or more sensors 1512, speaker 1514, and microphone 1516. Display 1510 is configured to output visual information (e.g., a graphical user interface (GUI) generated and/or rendered by processors 1504). In some embodiments, display 1510 is a touch screen that is configured to also receive touch-based input. Display 1510 may be implemented using liquid crystal display (LCD) technology, light-emitting diode (LED) technology, organic LED (OLED) technology, organic electro luminescence (OEL) technology, or any other type of display technologies. Sensors 1512 may include any number of different types of sensors for measuring a physical quantity (e.g., temperature, force, pressure, acceleration, orientation, light, radiation, etc.). Speaker 1514 is configured to output audio information and microphone 1516 is configured to receive audio input. One of ordinary skill in the art will appreciate that I/O system 1508 may include any number of additional, fewer, and/or different components. For instance, I/O system 1508 may include a keypad or keyboard for receiving input, a port for transmitting data, receiving data and/or power, and/or communicating with another device or component, an image capture component for capturing photos and/or videos, etc.

Communication system 1518 serves as an interface for receiving data from, and transmitting data to, other devices, computer systems, and networks. For example, communication system 1518 may allow computing device 1500 to connect to one or more devices via a network (e.g., a personal area network (PAN), a local area network (LAN), a storage area network (SAN), a campus area network (CAN), a metropolitan area network (MAN), a wide area network (WAN), a global area network (GAN), an intranet, the Internet, a network of any number of different types of networks, etc.). Communication system 1518 can include any number of different communication components. Examples of such components may include radio frequency (RF) transceiver components for accessing wireless voice and/or data networks (e.g., using cellular technologies such as 2G, 3G, 4G, 5G, etc., wireless data technologies such as Wi-Fi, Bluetooth, ZigBee, etc., or any combination thereof), global positioning system (GPS) receiver components, and/or other components. In some embodiments, communication system 1518 may provide components configured for wired communication (e.g., Ethernet) in addition to or instead of components configured for wireless communication.

Storage system 1520 handles the storage and management of data for computing device 1500. Storage system 1520 may be implemented by one or more non-transitory machine-readable mediums that are configured to store software (e.g., programs, code modules, data constructs, instructions, etc.) and store data used for, or generated during, the execution of the software.

In this example, storage system 1520 includes operating system 1522, one or more applications 1524, I/O module 1526, and communication module 1528. Operating system 1522 includes various procedures, sets of instructions, software components and/or drivers for controlling and managing general system tasks (e.g., memory management, storage device control, power management, etc.) and facilitates communication between various hardware and software components. Operating system 1522 may be one of various versions of Microsoft Windows, Apple Mac OS, Apple OS X, Apple macOS, and/or Linux operating systems, a variety of commercially-available UNIX or UNIX-like operating systems (including without limitation the variety of GNU/Linux operating systems, the Google Chrome® OS, and the like) and/or mobile operating systems such as Apple iOS, Windows Phone, Windows Mobile, Android, BlackBerry OS, Blackberry 10, and Palm OS, WebOS operating systems.

Applications 1524 can include any number of different applications installed on computing device 1500. Examples of such applications may include a browser application, an address book application, a contact list application, an email application, an instant messaging application, a word processing application, JAVA-enabled applications, an encryption application, a digital rights management application, a voice recognition application, location determination application, a mapping application, a music player application, etc.

I/O module 1526 manages information received via input components (e.g., display 1510, sensors 1512, and microphone 1516) and information to be outputted via output components (e.g., display 1510 and speaker 1514). Communication module 1528 facilitates communication with other devices via communication system 1518 and includes various software components for handling data received from communication system 1518.

One of ordinary skill in the art will realize that the architecture shown in FIG. 15 is only an example architecture of computing device 1500, and that computing device 1500 may have additional or fewer components than shown, or a different configuration of components. The various components shown in FIG. 15 may be implemented in hardware, software, firmware or any combination thereof, including one or more signal processing and/or application specific integrated circuits.

Figure 16:
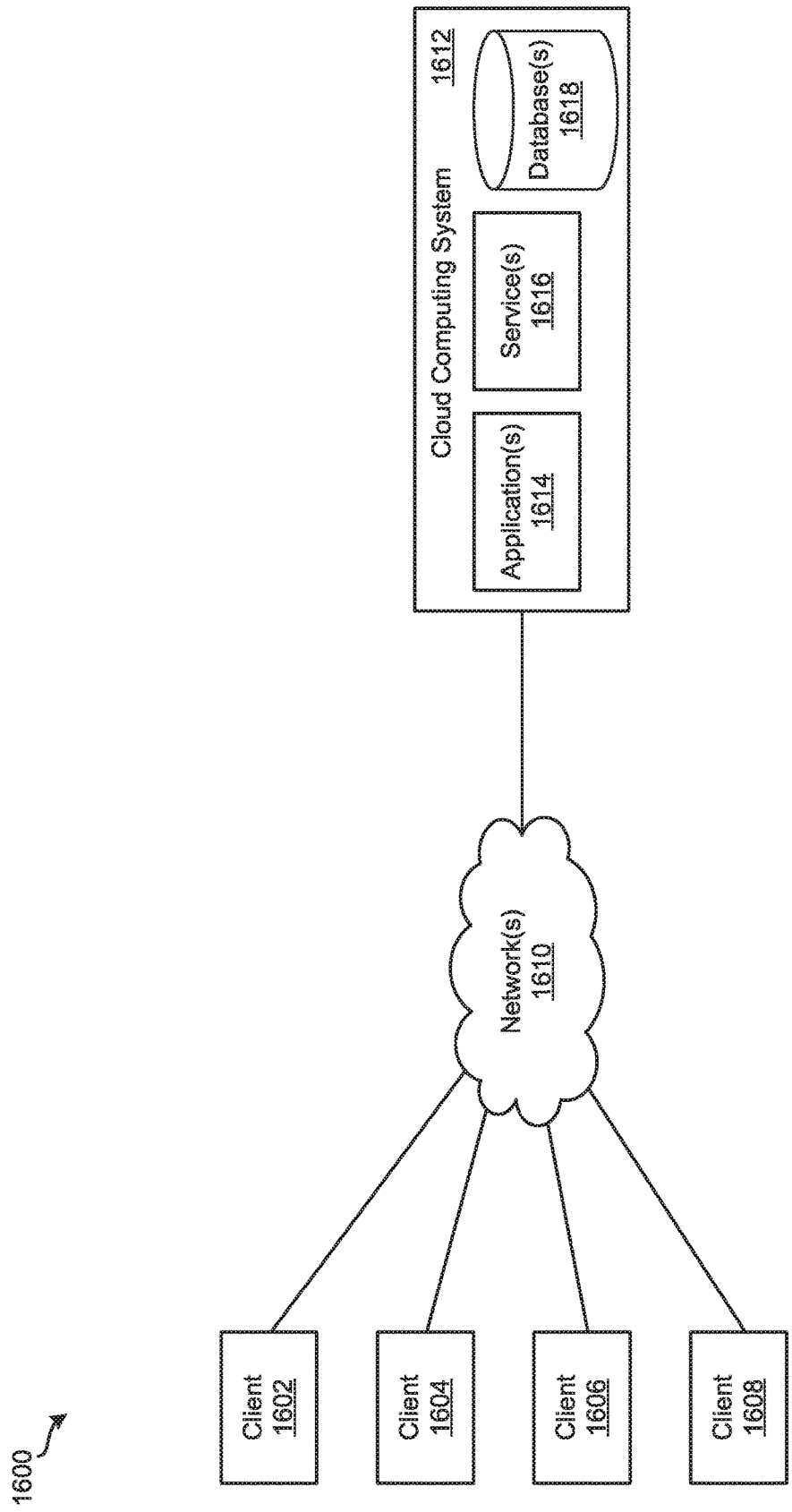
FIG. 16 illustrates an exemplary system, in which various embodiments may be implemented.

FIG. 16 illustrates an exemplary system 1600 for implementing various embodiments described above. For example, client devices 1602-1608 may be used to implement client devices 105*a-n* and cloud computing system 1612 may be used to implement computing system 110. As shown, system 1600 includes client devices 1602-1608, one or more networks 1610, and cloud computing system 1612. Cloud computing system 1612 is configured to provide resources and data to client devices 1602-1608 via networks 1610. In some embodiments, cloud computing system 1600 provides resources to any number of different users (e.g., customers, tenants, organizations, etc.). Cloud computing system 1612 may be implemented by one or more computer systems (e.g., servers), virtual machines operating on a computer system, or a combination thereof.

As shown, cloud computing system 1612 includes one or more applications 1614, one or more services 1616, and one or more databases 1618. Cloud computing system 1600 may provide applications 1614, services 1616, and databases 1618 to any number of different customers in a self-service, subscription-based, elastically scalable, reliable, highly available, and secure manner.

In some embodiments, cloud computing system 1600 may be adapted to automatically provision, manage, and track a customer's subscriptions to services offered by cloud computing system 1600. Cloud computing system 1600 may provide cloud services via different deployment models. For example, cloud services may be provided under a public cloud model in which cloud computing system 1600 is owned by an organization selling cloud services and the cloud services are made available to the general public or different industry enterprises. As another example, cloud services may be provided under a private cloud model in which cloud computing system 1600 is operated solely for a single organization and may provide cloud services for one or more entities within the organization. The cloud services may also be provided under a community cloud model in which cloud computing system 1600 and the cloud services provided by cloud computing system 1600 are shared by several organizations in a related community. The cloud services may also be provided under a hybrid cloud model, which is a combination of two or more of the aforementioned different models.

In some instances, any one of applications 1614, services 1616, and databases 1618 made available to client devices 1602-1608 via networks 1610 from cloud computing system 1600 is referred to as a "cloud service." Typically, servers and systems that make up cloud computing system 1600 are different from the on-premises servers and systems of a customer. For example, cloud computing system 1600 may host an application and a user of one of client devices 1602-1608 may order and use the application via networks 1610.

Applications 1614 may include software applications that are configured to execute on cloud computing system 1612 (e.g., a computer system or a virtual machine operating on a computer system) and be accessed, controlled, managed, etc. via client devices 1602-1608. In some embodiments, applications 1614 may include server applications and/or mid-tier applications (e.g., HTTP (hypertext transport protocol) server applications, FTP (file transfer protocol) server applications, CGI (common gateway interface) server applications, JAVA server applications, etc.). Services 1616 are software components, modules, application, etc. that are configured to execute on cloud computing system 1612 and provide functionalities to client devices 1602-1608 via networks 1610. Services 1616 may be web-based services or on-demand cloud services.

Databases 1618 are configured to store and/or manage data that is accessed by applications 1614, services 1616, and/or client devices 1602-1608. Databases 1618 may reside on a non-transitory storage medium local to (and/or resident in) cloud computing system 1612, in a storage-area network (SAN), on a non-transitory storage medium local located remotely from cloud computing system 1612. In some embodiments, databases 1618 may include relational databases that are managed by a relational database management system (RDBMS). Databases 1618 may be a column-oriented databases, row-oriented databases, or a combination thereof. In some embodiments, some or all of databases 1618 are in-memory databases. That is, in some such embodiments, data for databases 1618 are stored and managed in memory (e.g., random access memory (RAM)).

Client devices 1602-1608 are configured to execute and operate a client application (e.g., a web browser, a proprietary client application, etc.) that communicates with applications 1614, services 1616, and/or databases 1618 via networks 1610. This way, client devices 1602-1608 may access the various functionalities provided by applications 1614, services 1616, and databases 1618 while applications 1614, services 1616, and databases 1618 are operating (e.g., hosted) on cloud computing system 1600. Client devices 1602-1608 may be computer system 1400 or computing device 1500, as described above by reference to FIGS. 14 and 15, respectively. Although system 1600 is shown with four client devices, any number of client devices may be supported.

Networks 1610 may be any type of network configured to facilitate data communications among client devices 1602-1608 and cloud computing system 1612 using any of a variety of network protocols. Networks 1610 may be a personal area network (PAN), a local area network (LAN), a storage area network (SAN), a campus area network (CAN), a metropolitan area network (MAN), a wide area network (WAN), a global area network (GAN), an intranet, the Internet, a network of any number of different types of networks, etc.

FURTHER EXAMPLE EMBODIMENTS

Example 1

In one embodiment, the present disclosure includes a method for extracting information from clinical documents, the method comprising: receiving, by a computer system, machine-readable versions of said clinical documents; sectionalizing the clinical documents based on a plurality of machine learning (ML) algorithms, wherein one or more first ML algorithms classify different sections of the clinical documents based on significant signatures corresponding to the different sections, and wherein one or more second ML algorithms verify said classifications of the different sections based on text associated with the particular sections; transforming text associated with the sections into a plurality of structured clinical data records, wherein different words or phrases of text for each section are classified using a plurality of third ML algorithms selected based on said classification of each section, and wherein different combinations of classified words or phrases of the text for each particular section are mapped to a particular structured clinical data records; and storing information from the structured clinical data records in a searchable data structure.

In another embodiment, the present disclosure includes a non-transitory computer readable medium having stored thereon program code executable by a computer system, the program code comprising: code that causes the computer system to receive machine-readable versions of said clinical documents; code that causes the computer system to sectionalize the clinical documents based on a plurality of machine learning (ML) algorithms, wherein one or more first ML algorithms classify different sections of the clinical documents based on significant signatures corresponding to the different sections, and wherein one or more second ML algorithms verify said classifications of the different sections based on text associated with the particular sections; code that causes the computer system to transform text associated with the sections into a plurality of structured clinical data records, wherein different words or phrases of text for each section are classified using a plurality of third ML algorithms selected based on said classification of each section, and wherein different combinations of classified words or phrases of the text for each particular section are mapped to a particular structured clinical data records; and code that causes the computer system to store information from the structured clinical data records in a searchable data structure.

In another embodiment, the present disclosure includes computer system comprising: at least one processor; and a memory having stored thereon program code that, when executed by the at least one processor, causes the processor to: receive machine-readable versions of said clinical documents; sectionalize the clinical documents based on a plurality of machine learning (ML) algorithms, wherein one or more first ML algorithms classify different sections of the clinical documents based on significant signatures corresponding to the different sections, and wherein one or more second ML algorithms verify said classifications of the different sections based on text associated with the particular sections; transform text associated with the sections into a plurality of structured clinical data records, wherein different words or phrases of text for each section are classified using a plurality of third ML algorithms selected based on said classification of each section, and wherein different combinations of classified words or phrases of the text for each particular section are mapped to a particular structured clinical data records; and store information from the structured clinical data records in a searchable data structure.

The following additional features may apply in various combinations.

In one embodiment, receiving said clinical documents is in response to a patient-initiated request.

In one embodiment, sectionalizing comprises selecting the one or more second ML algorithms from a plurality of ML algorithms based on the classification by the one or more first ML algorithms.

In one embodiment, sectionalizing further comprises processing text associated with different sections having different classifications using different second NLP algorithms.

In one embodiment, the one or more ML algorithms selected are one or more of: a clinical entity NLP algorithm, a cancer entity NLP algorithm, a demographic entity NLP algorithm, a demographic ML model, a provider entity NLP algorithm, and a provider ML model.

In one embodiment, the one or more second ML algorithms comprise a combination of at least one machine learning (ML) model and at least one NLP algorithm.

In one embodiment, the one or more clinical documents include one or more sections comprising a plurality of subsections, wherein one or more third ML algorithms classify different subsections of the clinical documents based on subsection significant signatures corresponding to the different subsections, and wherein one or more fourth ML algorithms verify said classification of the different subsections based on text associated with the particular subsection.

In one embodiment, text associated with sections having a first classification is classified using a first set of NLP algorithms of the plurality of third ML algorithms and wherein text associated with sections having a second classification is classified using a second set NLP algorithms of the plurality of third ML algorithms.

In one embodiment, the plurality of third ML algorithms selected based on said classification of each section comprises one or more of: a clinical entity NLP algorithm, a cancer entity NLP algorithm, a demographic entity NLP algorithm, a demographic ML model, a provider entity NLP algorithm, and a provider ML model.

In one embodiment, the plurality of third ML algorithms selected based on said classification of each section comprises a first NLP algorithm for recognizing clinical entities comprising one or more of: medications, conditions, labs, procedures, diagnosis, vitals, allergies, treatments and genomic alterations.

In one embodiment, mapping comprises sending the classified words or phrases of the text for each particular section to a terminology service to determine medical codes.

In one embodiment, the structured clinical data records comprising one or more medical codes retrieved from a data store based on one or more classifications of the words or phrases of the text, and wherein the one or more medical codes are associated with one or more of the words or phrases of the text.

In one embodiment, one or more NLP algorithms for recognizing clinical entities is included in said one or more second ML algorithms and said plurality of third ML algorithms.

In one embodiment, the searchable data structure is a graph data structure.

In one embodiment, the graph data structure comprises nodes corresponding to patients and nodes corresponding to one or more of: a patient, a procedure, a condition, a provider, and a medication.

In one embodiment, the graph data structure comprises edges describing a relationship between a patient node and another node corresponding to a clinical concept or clinical domain of a plurality of predefined clinical concepts or clinical domains.

In one embodiment, the graph data structure comprises edges having at least one probability attribute.

In one embodiment, the method or program code further modifying the probabilities of a plurality of edges based on analysis of edges between a same type of nodes.

Example 2

In another embodiment, the present disclosure includes a method for sectionalizing a clinical document, the method comprising: receiving, by a computer system, a machine-readable version of the clinical document; identifying, by the computer system, one or more significant signatures in the machine-readable version of the clinical document, each significant signature corresponding to a possible section header in the clinical document; dividing, by the computer system, the clinical document into a plurality of sections based on the one or more significant signatures; for each of the plurality of sections, determining, by the computer system, a classification for the section, wherein the classification corresponds to a clinical concept or clinical domain selected from among a predefined list of clinical concepts or clinical domains, and wherein the determining of the classification is based on a machine learning (ML)-based analysis of: a significant signature associated with the section; and a body of the section; and recording, by the computer system, information regarding the plurality of sections and their respective classifications in a data structure.

In another embodiment, the present disclosure includes a non-transitory computer readable medium having stored thereon program code executable by a computer system for sectionalizing a clinical document, the program code comprising: code that causes the computer system to receive a machine-readable version of the clinical document; code that causes the computer system to identify one or more significant signatures in the machine-readable version of the clinical document, each significant signature corresponding to a possible section header in the clinical document; code that causes the computer system to divide the clinical document into a plurality of sections based on the one or more significant signatures; for each of the plurality of sections, code that causes the computer system to determine a classification for the section, wherein the classification corresponds to a clinical concept or clinical domain selected from among a predefined list of clinical concepts or clinical domains, and wherein the determining of the classification is based on a machine learning (ML)-based analysis of: a significant signature associated with the section; and a body of the section; and code that causes the computer system to record information regarding the plurality of sections and their respective classifications in a data structure.

In another embodiment, the present disclosure includes computer system comprising: at least one processor; and a memory having stored thereon program code that, when executed by the at least one processor, causes the processor to: receive a machine-readable version of a clinical document; identify one or more significant signatures in the machine-readable version of the clinical document, each significant signature corresponding to a possible section header in the clinical document; divide the clinical document into a plurality of sections based on the one or more significant signatures; for each of the plurality of sections, determine a classification for the section, wherein the classification corresponds to a clinical concept or clinical domain selected from among a predefined list of clinical concepts or clinical domains, and wherein the determining of the classification is based on a machine learning (ML)- based analysis of: a significant signature associated with the section; and a body of the section; and record information regarding the plurality of sections and their respective classifications in a data structure.

The following additional features may apply in various combinations.

In one embodiment, the method or computer code further comprising transmitting the data structure to a service configured to extract clinical information from each of the plurality of sections in the clinical document based on their respective classifications.

In one embodiment, identifying the one or more significant signatures comprises: identifying one or more text strings in the machine-readable version of the clinical document that exhibit a predefined set of formatting properties.

In one embodiment, the predefined set of formatting properties comprises formatting properties commonly exhibited by headers in a document.

In one embodiment, the predefined set of formatting properties include a property based on font style, font size, font position, or font color.

In one embodiment, dividing the clinical document into a plurality of sections based on the one or more significant signatures comprises: determining spans of content in the clinical document between consecutive significant signatures; and defining each span of content as a section in the plurality of sections.

In one embodiment, the predefined list of clinical concepts or clinical domains includes one or more of: medications, diagnosis, procedure, lab result, gene report, vitals, allergies, and immunizations.

In one embodiment, determining the classification for the section comprises:

providing textual content of the significant signature as input into one or more first ML algorithms.

In one embodiment, the one or more first ML algorithms are configured to output a candidate classification for the section based on the textual content of the significant signature.

In one embodiment, determining the classification for the section further comprises: analyzing textual content in the body of the section; and identifying, using one or more second ML algorithms, one or more clinical entities in the textual content of the body.

In one embodiment, the one or more identified clinical entities are verified by: passing each identified clinical entity and one or more words from the textual content that are associated with the identified clinical entity to a terminology service, wherein the terminology service is configured to perform a lookup of the one or more words in a clinical database corresponding to the identified clinical entity.

In one embodiment, determining the classification for the section further comprises: providing the candidate classification and the one or more identified clinical entities as input into one or more third ML algorithms.

In one embodiment, the one or more third ML algorithms are configured to output a final classification for the section based on the candidate classification and the one or more identified clinical entities.

In one embodiment, the one or more third ML algorithms are further configured to output a confidence score associated with the final classification.

In one embodiment, the machine-readable version of the clinical document comprises a plurality of pages, and wherein the identifying, the dividing, and the determining are performed on a page-by-page basis with respect to each of the plurality of pages.

In one embodiment, if a last section of one page in the plurality of pages shares a same classification with a first section of an immediately subsequent page in the plurality of pages and if the immediately subsequent page does not include a significant signature at its start, the last section and the first section are merged into a single section.

Example 3

In another embodiment, the present disclosure includes method comprising: receiving a clinical document partitioned into a set of sections, each section in the set of sections comprising a plurality of terms; identifying a section in the set of sections; determining a subset of a plurality of entity recognizers based on a classification of the section, each entity recognizer in the plurality of entity recognizers configured to identify terms in the section as being associated with a particular type of data; sending the section to the subset of the entity recognizers for processing; and generating a clinical statement based on terms identified in the section by the subset of the plurality of entity recognizers.

In another embodiment, the present disclosure includes a non-transitory machine-readable medium storing a program executable by at least one processor of a device, the program comprising sets of instructions for: receiving a clinical document partitioned into a set of sections, each section in the set of sections comprising a plurality of terms; identifying a section in the set of sections; determining a subset of a plurality of entity recognizers based on a classification of the section, each entity recognizer in the plurality of entity recognizers configured to identify terms in the section as being associated with a particular type of data; sending the section to the subset of the entity recognizers for processing; and generating a clinical statement based on terms identified in the section by the subset of the plurality of entity recognizers.

In another embodiment, the present disclosure includes system comprising: at least one processor; and a memory having stored thereon program code that, when executed by the at least one processor, causes the processor to: receive a clinical document partitioned into a set of sections, each section in the set of sections comprising a plurality of terms; identify a section in the set of sections; determine a subset of a plurality of entity recognizers based on a classification of the section, each entity recognizer in the plurality of entity recognizers configured to identify terms in the section as being associated with a particular type of data; send the section to the subset of the entity recognizers for processing; and generate a clinical statement based on terms identified in the section by the subset of the plurality of entity recognizers.

The following additional features may apply in various combinations.

In one embodiment, the program or method further comprising sending the section to a terminology service for processing, the terminology service configured to determine medical codes based on the section and associating the medical codes with a subset of the terms identified in the section by the plurality of entity recognizers; and receiving the section from the terminology service with the medical codes associated with the subset of the terms.

In one embodiment, the program or method further comprising: receiving a section classification map associated with the clinical document; and determining the classification of the section based on the section classification map.

In one embodiment, the program further comprising sending the clinical statement to an aggregation service for processing.

In one embodiment, the subset of the plurality of entity recognizers is a first subset of the plurality of entity recognizers, wherein the first subset of the plurality of entity recognizers is included in a first natural language processing (NLP) pipeline, wherein the program or method further comprising: determining a second subset of the plurality of entity recognizers based on the classification of the section; and sending the section to the second subset of the entity recognizers for processing, wherein generating the clinical statement is further based on terms identified in the section by the second subset of the plurality of entity recognizers.

In one embodiment, the clinical statement is a first clinical statement, wherein the program or method further comprising generating a second clinical statement based on terms identified in the section by the subset of the plurality of entity recognizers.

In one embodiment, the section is a first section in the set of sections, wherein the subset of the plurality of entity recognizers is a first subset of the plurality of entity recognizers, wherein the clinical statement is a first clinical statement, wherein the program or method further comprising: identifying a second section in the set of sections; determining a second subset of the plurality of entity recognizers based on a classification of the second section; sending the second section to the second subset of the entity recognizers for processing; and generating a second clinical statement based on terms identified in the second section by the second subset of the plurality of entity recognizers.

The various components and blocks shown above in the various figures may be implemented in software, for example, and may be embodied in computer executable program code that may be stored in a memory and executed by at least one processor, for example.

The above description illustrates various embodiments of the present disclosure along with examples of how aspects of the particular embodiments may be implemented. The above examples should not be deemed to be the only embodiments, and are presented to illustrate the flexibility and advantages of the particular embodiments as defined by the following claims. Based on the above disclosure and the following claims, other arrangements, embodiments, implementations and equivalents may be employed without departing from the scope of the present disclosure as defined by the claims.

What is claimed is:

1. A method comprising:
   receiving, by a computer system, a machine-readable clinical document;
   for each page of the clinical document:
      identifying one or more section header candidates in the page;
      for each section header candidate:
         attempting to classify the section header candidate as corresponding to one of a plurality of section types using a first classifier, wherein the first classifier maps non-clinical text to the plurality of section types; and
         if the attempting to classify using the first classifier is unsuccessful, attempting to the classify the section header candidate as corresponding to one of the plurality of section types using a second classifier different from the first classifier, wherein the second classifier recognizes one or more clinical entities;
      partitioning the page into one or more sections based on corresponding section header candidates that have been successfully classified using either the first classifier or the second classifier, the partitioning including associating each section with a section type in the plurality of section types in accordance with the classification of the section's corresponding section header candidate; and
      for each section, validating the section's section type by using a third classifier operating on a body of the section and comparing a classification of the body of the section with the classification of the section's corresponding section header candidate; and
   aggregating section information for each page of the clinical document into a section map data structure, the section information for each page including the one or more sections of the page and the section type of each of the one or more sections.

2. The method of claim 1 further comprising outputting the section map data structure to a service configured to extract clinical information from each section in the clinical document based on the section's section type.

3. The method of claim 1 wherein the first classifier employs a machine learning (ML) model trained to map non-clinical text to the plurality of section types, and wherein the second classifier employs a natural language processing (NLP) engine that performs clinical entity recognition.

4. The method of claim 1 wherein identifying the one or more section header candidates comprises:
   calculating an entropy score for each line of text in the page, wherein the entropy score is computed as a weighted average of one or more values of one or more stylistic or structural attributes of the line.

5. The method of claim 1 wherein identifying the one or more section header candidates comprises:
   determining a section hierarchy level for each section header candidate within the clinical document.

6. The method of claim 1 wherein attempting to classify the section header candidate using the first classifier comprises:
   providing the section header candidate as input to a machine learning (ML) model; and
   receiving, from the ML model, a plurality of confidence scores, each confidence score indicating a likelihood that the section header candidate can be classified as corresponding to a section type in the plurality of section types.

7. The method of claim 6 wherein attempting to classify the section header candidate using the first classifier further comprises:
   if one or more of the plurality of confidence scores exceeds a threshold, selecting the section type associated with the highest confidence score as a classified section type for the section header candidate.

8. The method of claim 6 wherein attempting to classify the section header candidate using the first classifier further comprises:
   if one or more of the plurality of confidence scores does not exceed a threshold, determining that the section header candidate cannot be classified using the first classifier.

9. The method of claim 1 wherein attempting to classify the section header candidate using the second classifier comprises:
   providing the section header candidate to a natural language processing (NLP) engine; and receiving, from the NLP engine, a list of one or more clinical entities and corresponding text terms found in the section header candidate.

10. The method of claim 9 wherein attempting to classify the section header candidate using the second classifier further comprises:
providing the list of the one or more clinical entities and corresponding text terms to a terminology service; and
receiving from the terminology service a list of confidence scores, each confidence score indicating, for a clinical entity in the list of one or more clinical entities, a likelihood that the clinical entity correctly matches its corresponding text term.

11. The method of claim 10 wherein the terminology service generates the list of confidence scores by consulting one or more clinical terminology databases.

12. The method of claim 1 wherein the third classifier is a natural language processing (NLP) engine, and using the third classifier comprises:
providing text of the body to the NLP engine;
receiving, from the NLP engine, a list of one or more clinical entities and corresponding text terms found in the text of the body;
providing the list of the one or more clinical entities and corresponding text terms to a terminology service; and
receiving from the terminology service a list of confidence scores, each confidence score indicating, for a clinical entity in the list of one or more clinical entities, a likelihood that the clinical entity correctly matches its corresponding text term.

13. The method of claim 12 wherein using the third classifier further comprises:
generating a clinical entity data structure for the body including (1) clinical entities found by the NLP engine in the text of the body and confirmed to be correct via an evaluation of the list of confidence scores received from the terminology service, and (2) for each clinical entity in (1), an appearance score indicating a percentage of confirmed clinical entity instances found in the text of the body that are instances of said each clinical entity.

14. The method of claim 13 wherein comparing a classification of the body of the section with the classification of the section's corresponding section header candidate further comprises:
evaluating the clinical entity data structure for the body against the section type and confidence score for the section using one or more roll-up rules; and
modifying the section type or the confidence score for the section if dictated by the evaluating.

15. The method of claim 1 further comprising, for each pair of consecutive pages in the clinical document:
determining whether a span of content on a second page of the pair is not a part of any section defined in the section map data structure; and
if the determining results in an answer of yes, checking whether the span of content can be classified as corresponding to a first section type that is consistent with a second section type of a last section of a first page of the pair.

16. The method of claim 15 wherein if the checking results in an answer of yes, merging the span of content into the last section of the first page.

17. The method of claim 1 wherein the plurality of section types includes one or more of: medications, diagnosis, procedure, lab result, gene report, vitals, allergies, and immunizations.

18. A non-transitory computer readable storage medium having stored thereon program code that, when executed by a computer system, causes the computer system to perform operations comprising:
receiving a machine-readable clinical document;
for each page of the clinical document:
identifying one or more section header candidates in the page;
for each section header candidate:
attempting to classify the section header candidate as corresponding to one of a plurality of section types using a first classifier, wherein the first classifier maps non-clinical text to the plurality of section types; and
if the attempting to classify using the first classifier is unsuccessful, attempting to the classify the section header candidate as corresponding to one of the plurality of section types using a second classifier different from the first classifier, wherein the second classifier recognizes one or more clinical entities;
partitioning the page into one or more sections based on corresponding section header candidates that have been successfully classified using either the first classifier or the second classifier, the partitioning including associating each section with a section type in the plurality of section types in accordance with the classification of the section's corresponding section header candidate; and
for each section, validating the section's section type by using a third classifier operating on a body of the section and comparing a classification of the body of the section with the classification of the section's corresponding section header candidate; and
aggregating section information for each page of the clinical document into a section map data structure, the section information for each page including the one or more sections of the page and the section type of each of the one or more sections.

19. A computer system comprising:
a processor; and
a memory having stored thereon program code that, when executed by the processor, causes the processor to:
receive a machine-readable clinical document;
for each page of the clinical document:
identify one or more section header candidates in the page;
for each section header candidate:
attempt to classify the section header candidate as corresponding to one of a plurality of section types using a first classifier, the first classifier employing a machine learning (ML) model trained to map non-clinical text to the plurality of section types; and
if the attempting to classify using the first classifier is unsuccessful, attempt to the classify the section header candidate as corresponding to one of the plurality of section types using a second classifier different from the first classifier, the second classifier employing a natural language processing (NLP) engine trained to perform clinical entity recognition;
partition the page into one or more sections based on corresponding section header candidates that have been successfully classified using either the first classifier or the second classifier, the partitioning including associating each section with a section type in the plurality of section types in accordance with the classification of the section's corresponding section header candidate; and for each section, validate the section's section type by using a third classifier operating on a body of the section and comparing a classification of the body of the section with the classification of the section's corresponding section header candidate; and aggregate section information for each page of the clinical document into a section map data structure, the section information for each page including the one or more sections of the page and the section type of each of the one or more sections.

20. The non-transitory computer readable storage medium of claim 18, the operations further comprising outputting the section map data structure to a service configured to extract clinical information from each section in the clinical document based on the section's section type.

21. The non-transitory computer readable storage medium of claim 18 wherein the first classifier employs a machine learning (ML) model trained to map non-clinical text to the plurality of section types, and wherein the second classifier employs a natural language processing (NLP) engine that performs clinical entity recognition.

22. The non-transitory computer readable storage medium of claim 18 wherein identifying the one or more section header candidates comprises:

calculating an entropy score for each line of text in the page, wherein the entropy score is computed as a weighted average of one or more values of one or more stylistic or structural attributes of the line.

23. The non-transitory computer readable storage medium of claim 18 wherein identifying the one or more section header candidates comprises:

determining a section hierarchy level for each section header candidate within the clinical document.

24. The non-transitory computer readable storage medium of claim 18 wherein attempting to classify the section header candidate using the first classifier comprises:

providing the section header candidate as input to a machine learning (ML) model; and
receiving, from the ML model, a plurality of confidence scores, each confidence score indicating a likelihood that the section header candidate can be classified as corresponding to a section type in the plurality of section types.

25. The non-transitory computer readable storage medium of claim 24 wherein attempting to classify the section header candidate using the first classifier further comprises:

if one or more of the plurality of confidence scores exceeds a threshold, selecting the section type associated with the highest confidence score as a classified section type for the section header candidate.

26. The non-transitory computer readable storage medium of claim 24 wherein attempting to classify the section header candidate using the first classifier further comprises:

if one or more of the plurality of confidence scores does not exceed a threshold, determining that the section header candidate cannot be classified using the first classifier.

27. The non-transitory computer readable storage medium of claim 18 wherein attempting to classify the section header candidate using the second classifier comprises:

providing the section header candidate to a natural language processing (NLP) engine; and receiving, from the NLP engine, a list of one or more clinical entities and corresponding text terms found in the section header candidate.

28. The non-transitory computer readable storage medium of claim 27 wherein attempting to classify the section header candidate using the second classifier further comprises:

providing the list of the one or more clinical entities and corresponding text terms to a terminology service; and
receiving from the terminology service a list of confidence scores, each confidence score indicating, for a clinical entity in the list of one or more clinical entities, a likelihood that the clinical entity correctly matches its corresponding text term.

29. The non-transitory computer readable storage medium of claim 18 wherein the third classifier is a natural language processing (NLP) engine, and using the third classifier comprises:

providing text of the body to the NLP engine;
receiving, from the NLP engine, a list of one or more clinical entities and corresponding text terms found in the text of the body;
providing the list of the one or more clinical entities and corresponding text terms to a terminology service; and
receiving from the terminology service a list of confidence scores, each confidence score indicating, for a clinical entity in the list of one or more clinical entities, a likelihood that the clinical entity correctly matches its corresponding text term.

30. The non-transitory computer readable storage medium of claim 29 wherein using the third classifier further comprises:

generating a clinical entity data structure for the body including (1) clinical entities found by the NLP engine in the text of the body and confirmed to be correct via an evaluation of the list of confidence scores received from the terminology service, and (2) for each clinical entity in (1), an appearance score indicating a percentage of confirmed clinical entity instances found in the text of the body that are instances of said each clinical entity.

31. The non-transitory computer readable storage medium of claim 30 wherein comparing a classification of the body of the section with the classification of the section's corresponding section header candidate further comprises:

evaluating the clinical entity data structure for the body against the section type and confidence score for the section using one or more roll-up rules; and
modifying the section type or the confidence score for the section if dictated by the evaluating.

32. The non-transitory computer readable storage medium of claim 18, the operations further comprising, for each pair of consecutive pages in the clinical document:

determining whether a span of content on a second page of the pair is not a part of any section defined in the section map data structure; and
if the determining results in an answer of yes, checking whether the span of content can be classified as corresponding to a first section type that is consistent with a second section type of a last section of a first page of the pair.

33. The non-transitory computer readable storage medium of claim 32 wherein if the checking results in an answer of yes, the operations further comprise merging the span of content into the last section of the first page.

34. The computer system of claim 19, wherein the program code further causes the processor to output the section map data structure to a service configured to extract clinical information from each section in the clinical document based on the section's section type.

35. The computer system of claim 19 wherein the program code that causes the processor to identify the one or more section header candidates comprises program code that, when executed, causes the processor to:
calculate an entropy score for each line of text in the page, wherein the entropy score is computed as a weighted average of one or more values of one or more stylistic or structural attributes of the line.

36. The computer system of claim 19 wherein the program code that causes the processor to identify the one or more section header candidates comprises program code that, when executed, causes the processor to:
determine a section hierarchy level for each section header candidate within the clinical document.

37. The computer system of claim 19 wherein the program code that causes the processor to attempt to classify the section header candidate using the first classifier comprises program code that, when executed, causes the processor to:
provide the section header candidate as input to a machine learning (ML) model; and
receive, from the ML model, a plurality of confidence scores, each confidence score indicating a likelihood that the section header candidate can be classified as corresponding to a section type in the plurality of section types.

38. The computer system of claim 37 wherein the program code that causes the processor to attempt to classify the section header candidate using the first classifier further comprises program code that, when executed, causes the processor to:
if one or more of the plurality of confidence scores exceeds a threshold, select the section type associated with the highest confidence score as a classified section type for the section header candidate.

39. The computer system of claim 37 wherein the program code that causes the processor to attempt to classify the section header candidate using the first classifier further comprises program code that, when executed, causes the processor to:
if one or more of the plurality of confidence scores does not exceed a threshold, determine that the section header candidate cannot be classified using the first classifier.

40. The computer system of claim 19 wherein the program code that causes the processor to attempt to classify the section header candidate using the second classifier further comprises program code that, when executed, causes the processor to:
provide the list of the one or more clinical entities and corresponding text terms to a terminology service; and
receive from the terminology service a list of confidence scores, each confidence score indicating, for a clinical entity in the list of one or more clinical entities, a likelihood that the clinical entity correctly matches its corresponding text term.

41. The computer system of claim 19 wherein the third classifier is a natural language processing (NLP) engine, and the program code that causes the processor to use the third classifier comprises program code that, when executed, causes the processor to:
provide text of the body to a natural language processing (NLP) engine;
receive, from the NLP engine, a list of one or more clinical entities and corresponding text terms found in the text of the body;
provide the list of the one or more clinical entities and corresponding text terms to a terminology service; and
receive from the terminology service a list of confidence scores, each confidence score indicating, for a clinical entity in the list of one or more clinical entities, a likelihood that the clinical entity correctly matches its corresponding text term.

42. The computer system of claim 41 wherein the program code that causes the processor to use the third classifier further comprises program code that, when executed, causes the processor to:
generate a clinical entity data structure for the body including (1) clinical entities found by the NLP engine in the text of the body and confirmed to be correct via an evaluation of the list of confidence scores received from the terminology service, and (2) for each clinical entity in (1), an appearance score indicating a percentage of confirmed clinical entity instances found in the text of the body that are instances of said each clinical entity.

43. The computer system of claim 42 wherein the program code that causes the processor to compare a classification of the body of the section with the classification of the section's corresponding section header candidate further comprises program code that, when executed, causes the processor to:
evaluate the clinical entity data structure for the body against the section type and confidence score for the section using one or more roll-up rules; and
modify the section type or the confidence score for the section if dictated by the evaluating.

44. The computer system of claim 19, the program code further causing the processor to, for each pair of consecutive pages in the clinical document:
determine whether a span of content on a second page of the pair is not a part of any section defined in the section map data structure; and
if the determining results in an answer of yes, check whether the span of content can be classified as corresponding to a first section type that is consistent with a second section type of a last section of a first page of the pair.

45. The computer system of claim 19 wherein if the checking results in an answer of yes, the program code further causes the processor to merge the span of content into the last section of the first page.

* * * * *